(12) United States Patent
Purdy et al.

(10) Patent No.: US 12,029,533 B2
(45) Date of Patent: Jul. 9, 2024

(54) BLOOD PRESSURE ANALYSIS SYSTEM AND METHOD

(71) Applicant: ENDOPHYS HOLDINGS, LLC, Dallas, TX (US)

(72) Inventors: Phillip Douglas Purdy, Maypearl, TX (US); Ronald Bruce Jennings, Plano, TX (US)

(73) Assignee: Endophys Holdings, LLC, Dallas, TX (US)

( * ) Notice: Subject to any disclaimer, the term of this patent is extended or adjusted under 35 U.S.C. 154(b) by 656 days.

(21) Appl. No.: 14/335,525

(22) Filed: Jul. 18, 2014

(65) Prior Publication Data
US 2015/0025396 A1    Jan. 22, 2015

Related U.S. Application Data

(60) Provisional application No. 61/847,847, filed on Jul. 18, 2013.

(51) Int. Cl.
*A61B 5/021*     (2006.01)
*A61B 5/00*      (2006.01)
(Continued)

(52) U.S. Cl.
CPC ........ *A61B 5/02108* (2013.01); *A61B 5/0215* (2013.01); *A61B 5/022* (2013.01);
(Continued)

(58) Field of Classification Search
None
See application file for complete search history.

(56) References Cited

U.S. PATENT DOCUMENTS

| 4,446,715 A | 5/1984 | Bailey |
| 4,691,708 A * | 9/1987 | Kane ................. A61B 5/02154 73/705 |

(Continued)

FOREIGN PATENT DOCUMENTS

| EP | 2299574 A2 | 3/2011 |
| WO | WO 93/10705 A1 | 6/1993 |

OTHER PUBLICATIONS

Hashemian et al., "Assessment of Fiber Optic Pressure Sensors", 1995, Analysis and Measurement Services Corporation (Year: 1995).*
(Continued)

*Primary Examiner* — Michael R Bloch
(74) *Attorney, Agent, or Firm* — James H. Ortega; David W. Carstens; Carstens, Allen & Gourley, LLP

(57) ABSTRACT

A blood pressure analysis system/method allowing conversion from an analog sensor input to a standardized analog output interface is disclosed. In some preferred embodiments the system/method permits a fiber optic pressure sensor to be interfaced to a standard patient care monitor (PCM) system using standardized Wheatstone Bridge analog interface inputs. Within this context the Wheatstone Bridge sensed output is defined by stimulus from the PCM and modulation of bridge element values by the conditioned output of an analog pressure sensor. The use of analog-to-digital-to-analog conversion in this blood pressure analysis permits retrofitting of PCM devices having analog Wheatstone Bridge inputs with advanced patient monitoring sensors without the need for specialized modifications to the baseline PCM data collection framework. Methods disclosed herein include techniques to connect arbitrary types/numbers of analog sensors to traditional PCM systems without the need for PCM system hardware/software modifications.

59 Claims, 16 Drawing Sheets

(51) Int. Cl.
  *A61B 5/0215* (2006.01)
  *A61B 5/022* (2006.01)
  *A61B 5/03* (2006.01)

(52) U.S. Cl.
  CPC ............ *A61B 5/036* (2013.01); *A61B 5/7235* (2013.01); *A61B 5/002* (2013.01); *A61B 5/02156* (2013.01); *A61B 5/02158* (2013.01); *A61B 2560/0223* (2013.01); *A61B 2560/0257* (2013.01); *A61B 2562/0247* (2013.01); *A61B 2562/0266* (2013.01); *A61B 2562/22* (2013.01); *A61B 2562/223* (2013.01); *A61B 2562/228* (2013.01)

(56) References Cited

U.S. PATENT DOCUMENTS

| | | | | |
|---|---|---|---|---|
| 4,703,757 | A | * | 11/1987 | Cohen ................ A61B 5/02154 73/705 |
| 4,705,047 | A | | 11/1987 | Bailey |
| 4,787,396 | A | * | 11/1988 | Pidorenko .......... A61B 5/02154 600/480 |
| 5,048,524 | A | | 9/1991 | Bailey |
| 5,325,865 | A | * | 7/1994 | Beckman ........... A61B 5/02154 250/214 C |
| 5,668,320 | A | | 9/1997 | Cowan |
| 5,987,995 | A | * | 11/1999 | Sawatari ............. A61B 5/0215 73/705 |
| 6,201,346 | B1 | | 4/2001 | Hall et al. |
| 7,724,148 | B2 | | 5/2010 | Samuelsson et al. |
| 7,946,997 | B2 | | 5/2011 | Hubinette |
| 8,066,681 | B1 | * | 11/2011 | Hall ..................... G01L 9/0079 604/264 |
| 2003/0045781 | A1 | | 3/2003 | Rosenheimer |
| 2004/0147847 | A1 | | 7/2004 | Ng et al. |
| 2007/0106165 | A1 | | 5/2007 | Tulkki |
| 2007/0112274 | A1 | | 5/2007 | Heitzmann et al. |
| 2007/0287924 | A1 | | 12/2007 | Glocker et al. |
| 2008/0100440 | A1 | * | 5/2008 | Downie ................ G06K 19/00 340/572.1 |
| 2008/0119758 | A1 | * | 5/2008 | Samuelsson ........... H04B 1/713 600/561 |
| 2008/0159738 | A1 | * | 7/2008 | Lavranchuk ......... G02B 6/3895 398/17 |
| 2008/0250341 | A1 | * | 10/2008 | Dlugos .............. A61B 5/02055 715/771 |
| 2010/0052863 | A1 | * | 3/2010 | Renfro, Jr. ......... G06K 7/10366 398/9 |
| 2010/0234698 | A1 | * | 9/2010 | Manstrom ............. A61M 5/007 600/301 |
| 2010/0286536 | A1 | | 11/2010 | Samuelsson et al. |
| 2011/0046477 | A1 | * | 2/2011 | Hulvershorn ........ A61B 5/0215 600/424 |
| 2012/0071744 | A1 | * | 3/2012 | Euliano, II ........... A61B 5/4362 600/382 |
| 2012/0123223 | A1 | | 5/2012 | Freeman et al. |
| 2012/0179012 | A1 | | 7/2012 | Saffarian |
| 2013/0131523 | A1 | * | 5/2013 | Suchecki ........... A61B 5/02007 600/486 |
| 2013/0225941 | A1 | * | 8/2013 | Samuelsson ......... A61B 5/6851 600/300 |

OTHER PUBLICATIONS

Extended European Search Report for European Application No. 14827043.2 dated Feb. 2, 2017.

* cited by examiner

*Prior Art*

US 12,029,533 B2

BLOOD PRESSURE ANALYSIS SYSTEM AND METHOD

CROSS REFERENCE TO RELATED APPLICATIONS

This application claims benefit and incorporates by reference United States Provisional patent application filed with the USPTO on 18 Jul. 2013, with Ser. No. 61/847,847.

PARTIAL WAIVER OF COPYRIGHT

All of the material in this patent application is subject to copyright protection under the copyright laws of the United States and of other countries. As of the first effective filing date of the present application, this material is protected as unpublished material.

However, permission to copy this material is hereby granted to the extent that the copyright owner has no objection to the facsimile reproduction by anyone of the patent documentation or patent disclosure, as it appears in the United States Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO A MICROFICHE APPENDIX

Not Applicable

FIELD OF THE INVENTION

The present invention generally relates to systems and methods for blood pressure analysis using analog sensor interfaces. While not limitive of the invention teachings, the present invention may in some circumstances have application to situations in which a wide variety of medical patient monitoring sensors (blood pressure sensors, cerebrospinal fluid sensors, etc.) used in monitoring patients within a healthcare environment are interfaced to computerized Patient Care Monitor (PCM) systems.

PRIOR ART AND BACKGROUND OF THE INVENTION

Prior Art System Overview (0100)

Existing blood pressure analysis systems that operate in the context of conventional patient care monitors (PCMs) are generally illustrated in FIG. 1 (0100). In this example, the patient (0101) is monitored using an analog sensor configured within a sensor bridge (0111). The analog sensor may comprise a wide variety of technologies and may be configured to sense a wide variety of patient conditions, including but not limited to blood pressure, temperature, etc. Within this context the sensor bridge (0111) is connected to a patient care monitor (PCM) (0112) that displays the current sensed status of the sensor bridge (0111) in response to excitation stimulus provided by the PCM (0112). The PCM system (0112) is often computerized and configured with software read from a computer readable medium (0113). Displays or other audio/video indicia within the PCM (0112) are interpreted by operators (0102) or other healthcare professionals.

Prior Art Method Overview (0200)

The prior art blood pressure analysis system illustrated in FIG. 1 (0100) typically has an associated data collection method as generally illustrated in FIG. 2 (0200) comprising the following instantaneous analog processing steps:
  (1) The analog sensor used to measure patient vital statistics is incorporated into a Wheatstone Bridge (0201);
  (2) The Wheatstone Bridge is excited via a voltage source from the PCM (0202);
  (3) The patient vital statistics are captured by the analog sensor within the Wheatstone Bridge (0203);
  (4) The Wheatstone Bridge characteristics are modulated by the patient analog sensor (0204);
  (5) The output of the Wheatstone Bridge is measured by the PCM and filtered/displayed on the PCM (0205); and
  (6) Control is continuously passed to step (2).

In most circumstances the configuration of the Wheatstone Bridge is standardized with respect to the class of PCM performing the measurement. Thus, industry standards typically dictate the configuration and characteristics of the Wheatstone Bridge, with the associated analog sensors being chosen to conform to these specifications.

Prior Art Patent Publications/Present Invention Comparison

Patents containing prior art that are relevant to the present invention can be seen in the following issued U.S. patents:
  NONINVASIVE BLOOD PRESSURE MONITORING SYSTEM, U.S. Pat. Nos. 7,503,897/7,361,147/7,318,807/7,144,372: These patents fundamentally describe devices that convert non-invasive blood pressure (NIBP) sensor signal which is derived from a pneumatic sensor into a signal that can be interfaced to an invasive blood pressure monitor input. In contrast to this prior art, the present invention describes an invasive fiber optic blood pressure sensor which employs a fiber optic sensor with an invasive blood pressure monitor input and provides other functionality not described by these patents. The present invention uniquely integrates the output from a fiber optic signal conditioner, that itself receives inputs from an optical pressure sensor apparatus, with the excitation voltage output from a physiological monitor originally designed to interface with a fluidic external pressure transducer and generates an input to that monitor consisting of an accurate replication of the inputs that would be received from a Wheatstone Bridge external pressure transducer.
  INTRACRANIAL PRESSURE MONITORING SYSTEM, U.S. Pat. No. 5,325,865: This patent describes an interface between an intracranial catheter mounted optical light emitting diode (LED) based pressure sensor and a patient care monitor (PCM). The device incorporates LED temperature compensation and uses the patient care monitor (PCM) excitation voltage for power. This prior art differs significantly from the present invention in that the present invention is based on fiber optic pressure transducers that are remotely stimulated by LEDs to excite the F-P cavity, does not require temperature compensation, and provides other functionality not described by this patent.

ARTERIAL LINE EMULATOR, U.S. Pat. No. 6,471,636: This patent describes a device that interfaces a non-invasive blood pressure monitor with and invasive blood pressure monitor. This patent disclosure significantly differs from the present invention in that the present invention interfaces an invasive fiber optic blood pressure sensor with an invasive blood pressure monitor input and provides other functionality not described by this patent.

SELF-POWERED INTERFACE CIRCUIT FOR USE WITH A TRANSDUCER SENSOR, U.S. Pat. No. 5,568,815: This patent describes an analog electronic device that interfaces a semiconductor transducer to a patient vital signs monitor. The semiconductor transducers described in this patent are configured in a Wheatstone Bridge circuit and the device is powered by the excitation voltage from the patient care monitor (PCM). This patent disclosure significantly differs from the present invention in that the present invention is based on fiber optic pressure transducers which are not based on a Wheatstone Bridge circuit, is implemented primarily using digital electronics, derives its power from batteries or utility AC power, and provides other functionality not described by this patent.

SIGNAL CONDITIONING DEVICE FOR INTERFACING INTRAVASCULAR SENSORS HAVING VARYING OPERATIONAL CHARACTERISTICS TO A PHYSIOLOGICAL MONITOR, U.S. Pat. No. 6,585,660: This patent describes a digital electronic device that is powered from a patient care monitor (PCM) excitation voltage and interfaces resistive sensor elements to a patient care monitor (PCM) with temperature compensating circuits. This patent disclosure significantly differs from the present invention in that the present invention is based on fiber optic pressure transducers which are not based on resistive sensor elements, derives its power from batteries or utility AC power, does not require temperature compensation, and provides other functionality not described by this patent.

None of these cited patents provides the capability of extending the range of existing PCM hardware by providing an interface to advanced analog sensor detection measurement systems.

Prior Art Deficiencies

The prior art blood pressure analysis system/method illustrated in FIG. 1 (0100) and FIG. 2 (0200) respectively suffer from a variety of drawbacks, including but not limited to the following:

Most PCMs define limits on the electrical characteristics of the Wheatstone Bridge, resulting in a narrowing of acceptable analog sensors that can be used with the PCM. Generally speaking, an arbitrary analog sensor cannot be connected to a PCM that requires a limited/fixed Wheatstone Bridge electrical interface.

PCMs generally do not support fiber optic based blood pressure sensors.

PCMs generally do not support multi-channel analog sensors within a single sensor input.

PCMs are generally not adaptable to new types of IBP analog sensors that are not compatible with Wheatstone Bridge sensing interfaces.

PCMs generally incorporate low pass filtering to address noise present in the patient environment, resulting in poor high frequency BP measurement characteristics.

PCMs generally are susceptible to low frequency power line interference.

PCMs are generally incompatible with use in a MRI imaging environment.

PCMs generally have a difficult time in discriminating blood pressure readings with low heart rates and/or low systolic/diastolic pressure ratios.

PCMs generally have a significant delay (multiple seconds) in displaying real-time data acquired from traditional BP sensors.

PCMs generally do not provide reference pressure signals in digital form for ancillary processing by an external computer system.

PCMs are less immune to electromagnetic interference due to the wired nature of their sensor-to-computer interface.

PCMs generally do not provide significant electrical isolation of the patient from the monitoring device. Generally speaking, the use of wired interconnects from the PCM to the patient often results in the potential for electromagnetic interference as well as an unwanted electrical path to the patient's body. Better isolation in the form of an optical interface is generally not possible using conventional PCM technologies.

PCMs are generally configured with firmware that lacks any ability for field modifications or field reprogramming.

PCMs cannot stream real-time digital and/or analog pressure data to a general remote computer system for ancillary processing. While some prior art systems do permit data streaming, this feature is limited to similarly configured instruments in the same product line and not to a general purpose data analysis computer.

PCMs lack support for real-time and/or post-processing of collected data.

Many PCMs lack portability and the ability for battery powered operation.

One skilled in the art will no doubt be able to determine other deficiencies in the prior art that have as yet to be addressed by the prior art.

OBJECTIVES OF THE INVENTION

Accordingly, the objectives of the present invention are (among others) to circumvent the deficiencies in the prior art and affect the following objectives:

(1) Provide for a blood pressure analysis system and method that permits a wide variety of analog sensor types to be interfaced to conventional PCM systems that require Wheatstone Bridge interfaces.

(2) Provide for a blood pressure analysis system and method that permits high performance sensors to be attached to conventional PCMs.

(3) Provide for a blood pressure analysis system and method that permits high sensitivity pressure sensors to be attached to conventional PCMs.

(4) Provide for a blood pressure analysis system and method that permits high sensitivity blood pressure sensors to be attached to conventional PCMs.

(5) Provide for a blood pressure analysis system and method that permits fiber optic blood pressure sensors to be attached to conventional PCMs.

(6) Provide for a blood pressure analysis system and method that permits blood pressure sensors having wider dynamic range to be attached to conventional PCMs.

(7) Provide for a blood pressure analysis system and method that permits blood pressure sensors having higher accuracy to be attached to conventional PCMs.

(8) Provide for a blood pressure analysis system and method that permits blood pressure sensors having smaller form factors to be attached to conventional PCMs.

(9) Provide for a blood pressure analysis system and method that permits multi-channel blood pressure sensors to be attached to conventional PCMs.

(10) Provide for a blood pressure analysis system and method that permits catheter-based blood pressure sensors to be attached to conventional PCMs.

(11) Provide for a blood pressure analysis system and method that permits neonatal blood pressure sensors to be attached to conventional PCMs.

(12) Provide for a blood pressure analysis system and method that permits use of Fabry-Perot pressure sensors to measure pressure within a medical context (blood pressure, etc.).

(13) Provide for a blood pressure analysis system and method that permits measurement of pressure using a Fabry-Perot pressure sensor positioned at the distal end of a medical device.

(14) Provide for a blood pressure analysis system and method that permits measurement of pressure using a Fabry-Perot pressure sensor positioned at the distal end of a medical device, the medical device selected from a group consisting of a catheter, catheter incorporating a mounted balloon, vascular sheath, ventriculostomy catheter, ventricular shunt catheter, lumbar drain, and intracranial pressure monitor structure.

While these objectives should not be understood to limit the teachings of the present invention, in general these objectives are achieved in part or in whole by the disclosed invention that is discussed in the following sections. One skilled in the art will no doubt be able to select aspects of the present invention as disclosed to affect any combination of the objectives described above.

Contrasting the Present Invention With the Prior Art

Many medical circumstances involve various forms of physiological monitoring. These include simple temperature measurement by placement of a thermometer under the tongue, blood pressure measurement using a sphygmomanometer (blood pressure cuff), or other external monitoring techniques. For conditions requiring more precise or intensive monitoring, mechanisms have evolved over many decades to use electronic means and more invasive access to patient physiology. In the case of temperature measurement, these include temperature probes that may be internal to the body or on the skin.

In the case of blood pressure measurement, the most common sensing means involves placement of a catheter structure (usually in tubing) within an arterial fluid column. This catheter structure incorporates an external transducer (that is integrated with a Wheatstone Bridge for interfacing to a patient care monitor (PCM)) and extends from the patient to an intravenous (IV) dispensing pole. If the transducer is at the level of the heart, it provides reasonably accurate measurements of blood pressure under normal physiological circumstances. Since it samples at the end of a fluid column, however, it is subject to sources of error (misplacement of the transducer on the IV pole at a level higher or lower than the heart, clotting or other impedance of the signal conduction through the tubing). A Wheatstone Bridge works by application of an electrical current of a known strength across a resistive circuit which alters resistive properties based on the amount of pressure applied to the circuitry. The transducer is "zeroed" to atmospheric pressure at the beginning of the monitoring session to adjust the pressure relative to ambient air pressure. Subsequently, when a different pressure is applied to the circuit, the returning voltage is measured and the pressure is calculated. This mechanism of monitoring is applied to radial artery catheter monitoring of blood pressure by anesthesiologists during surgery or other invasive procedures and in intensive care units in which hemodynamic instability is a concern.

More recently, an electronic circuit technology analogous to the Wheatstone Bridge has been applied to wire sensors placed in the body with the transducer circuitry placed directly on the wire (U.S. Patent Application Publication 2007/0106165 A1), in which a sensor wire assembly comprises a sensor element at the tip of a guide wire and wire connectors connected to the sensor element which supply an excitation voltage and a readout voltage which is altered from the excitation voltage by the pressure applied across the sensor. While this circuitry is analogous to the Wheatstone Bridge via application of an excitation voltage and reading of a returning voltage, it does not work precisely as a Wheatstone Bridge insofar as the input voltage is not required to be supplied by a patient care monitor (PCM) and hence there is adaptive circuitry implied to communicate from the sensor circuitry to the patient monitor circuitry. This circuitry may utilize the monitor's excitation voltage or may use a "signal adapting circuitry" that may display a human-readable output corresponding to the sensed pressure. This reference discloses a standardized output in the form of an analog voltage output signal. It also envisions a wireless form of communication (Bluetooth, etc.) between the sensor wire circuitry and a patient monitor circuitry. Under some embodiments, the reference discloses a sensor assembly utilizing an input electronic circuitry, an output electronic circuitry, and an electronic communication to a patient monitor, all of which are analog in nature and based on a continuous voltage and resistance circuitry, rather than discrete, digital observations of pressure that enable more sophisticated data analysis.

This is further described in U.S. Pat. No. 7,946,997, in which the wire sensor described in the earlier patent is claimed in relation to another signal adapting circuitry that sends the output from the sensor across optical communication channels and then converts the optical communication back into an electronic signal for communication to a patient monitor. Hence, the optical communication channel is used to transmit the analog data from its source to its analog output.

Other patents and filings (U.S. Patent Application Publication 2010/0286536 and U.S. Pat. No. 7,724,148 B2) describe transceiver units related to the wire sensors described in the earlier patents and hence are based on analog signal technology from the sensors. They describe a wireless link from a transceiver unit to a communication unit that obviates the need for a physical, wired connection.

While the technology described above utilizes sensors placed inside the body to measure pressure, they are based on electronic resistance technology analogous to that in the Wheatstone Bridge described earlier. Each uses an input electrical signal that is modified across a resistive circuit and the pressure is "sensed" along a waveform generated by the continuous electrical input signal, and hence it is not a set of discrete observations of pressure and is not amenable to digital data analysis.

In contrast, the present invention uses a technology for pressure sensing incorporating optical signals transmitted along optical fibers from a light source to a sensor (Fabry-Perot sensor) at the opposite end of the optical fiber. The light is transmitted as discrete pulsations at very high frequencies (1000 pulses per second and higher) which reflect from the diaphragm in the sensor and return to the proximal optical fiber and are detected as discrete observations of pressures. Each reading is assigned a value based on gauge (calibration) factors of the individual diaphragm (input from a memory unit specific to that diaphragm) and based on an observation of atmospheric pressure obtained prior to insertion of the sensor into the patient ("zeroing function"). In a presently preferred invention embodiment, two light pulses are needed to obtain one pressure observation, hence a pulse rate of 1000 Hz produces a pressure reading rate of 500 Hz, with accuracy of <1 mm Hg. This highly accurate, high-frequency, digital readout of intravascular pressure is possible when a sensor is inserted in a patient's artery and has multiple potential advantages analytically. It also is not inherently subject to signal filtration functions applied in standard patient monitors or to 60 Hz interference resulting from electronic signals based on alternating current electrical sources that may be proximal to the patient. However, the collection of digital data based on fiber optic sensor technology at high sampling rates is inherently dissimilar to that obtained via sensors based on analog electrical interference technology such as that in a Wheatstone Bridge and in the sensor technology disclosed above.

Another technology is described in U.S. Patent Application Publication 2007/0287924. In this reference, the signal from an analog sensor passes through an analog-to-digital converter (A/D converter) to produce a digital signal and that signal is transmitted to a second converter (D/A converter) that converts the digital signal into an appropriate analog signal based on the excitation voltage from the patient care monitor. This reference uses a different approach to conversion of an analog sensor signal with variable excitation voltages in its electronics into a signal that communicates with a patient care monitor. It would not be applicable to a technology in which the acquisition technology is a digital sensor technology, such as a Fabry-Perot fiber optic sensor. Additionally, this reference does not provide a means for digital output of the data—it is confined to analog-to-digital and then digital-to-analog circuitry specifically designed to convert a non-Wheatstone Bridge transducer sensor to a Wheatstone Bridge type signal.

Yet another technology is described in U.S. Patent Application Publication 2003/0045781 A1, in which a device for communication of output from medical sensors with patient care monitors is claimed. It constitutes another version of a Wheatstone Bridge emulator in which an electronic signal from an electronic sensor is amplified to match that expected from the excitation signal from a patient care monitor. Again, it is a means of converting from one type of analog signal to a different type of analog signal for means of displaying on a standard clinical monitor.

Fabry-Perot sensors have extensive prior art related to multiple configurations of sensors and their use in medicine and industry, both for temperature and for pressure measurements (see U.S. Pat. Nos. 4,329,058; 4,897,542; 5,297,437). While much of this basic intellectual property protection has expired, multiple variations on construction of sensors have been invented in recent years. However, variations on the structure of sensors or their light properties do not bear on the present invention, which envisions a plurality of potential sensor structures, all based on fiber optic sensor technology with digital output from the signal conditioners with which they are mated. The sensor particulars may all be adaptable to the data management described herein. The primary vascular use of Fabry-Perot sensors has historically been in intraortic balloon pumps, owing to their high sampling rate and high accuracy. However, their routine use in other applications has been hindered by their incompatibility with existing clinical care monitors. While existing Wheatstone Bridge and other electrically-actuated sensors deliver analog outputs compatible with or adaptable to clinical care monitors, the discretely sampled pressures with numerical digital outputs have heretofore not been displayed on clinical care monitors. While such display would have the advantage of utility with widely available monitors, fiber optic pressure sensors deliver information of such fidelity that degradation of the information to that displayed on monitors, combined with the more inexpensive and readily available Wheatstone Bridge technology which is matched to the patient care monitors in fidelity and sampling rate has been an economic impediment to implementation of the Fabry-Perot fiber optic technology in a wider clinical sphere.

The current invention addresses that technological gap by providing a means of conversion of the digital data acquired via a fiber optic Fabry-Perot sensor to an analog signal compatible with patient care monitors (PCMs) while maintaining a separate output (a USB port in some preferred invention embodiments) that transmits the full-fidelity data from the sensor to a device (computer, etc.) capable of higher-level analysis than that enabled by the analog output. Additionally, the present invention provides a display of pressure data taken directly from the fiber optic signal conditioner, thus showing the higher fidelity data acquired from the sensor, even under circumstances where a device may not be attached to the USB port or to the port for the patient care monitor. In a presently preferred embodiment, pressures are sampled at 1000 Hz frequency over four seconds, and the peak pressure during this time period is displayed as the systolic pressure, the trough pressure is displayed as the diastolic pressure, and the arithmetic mean of all pressure readings is displayed as the mean arterial pressure. The cycle refreshes every 4 seconds.

While Wheatstone Bridge emulation for electronic sensors may be construed to exist in prior art (U.S. Pat. No. 7,946,997 B2), such emulation in that disclosure involved the modification of the analog output from the sensor, based on its input current, to match the expected output to a clinical patient monitor, based on the excitation current from the monitor. That differs significantly from the algorithm required to convert the digital stream of data from a fiber optic Fabry-Perot sensor (using an interferometer or ratiometric approach) into an analog output in which the input current from the monitor is read and the numerical readings are converted to an output current that the monitor displays as though it were reading its input from a Wheatstone Bridge, such as is embodied in the current invention.

By achieving display of converted analog-to-digital output from the sensor, output to a patient care monitor through use of the Wheatstone Bridge transformation of the digital output described above, and direct streaming of data through a digital communications port (serial USB, in the current case), the present invention is both novel and more robust and flexible than other current pressure-sensing analytic technologies.

BRIEF SUMMARY OF THE INVENTION

System Overview

The present invention in various embodiments addresses one or more of the above described OBJECTIVES in the following manner. The present invention generally comprises an analog-to-digital-to-analog conversion process in which an analog sensor input is converted to digital and then compensated using calibration factors. The results of this compensated digital data are then converted to analog and presented to a Wheatstone Bridge emulator that receives excitation input from an external PCM (or other stimulus system). The excitation input from the PCM is modulated by the excitation input from the external PCM to emulate the characteristics of a conventional Wheatstone Bridge, resulting in a transparent presentation of the converted analog sensor data to the PCM for analysis/display. This analog-to-digital-to-analog conversion process permits high performance sensors to be attached to conventional PCM system hardware without the need for any PCM modifications. Additionally, individual analog sensor calibration factors ensures that the analog sensors need not be trimmed or compensated for by the PCM to ensure accurate measured sensor results.

Method Overview

The present invention system may be utilized in the context of an overall blood pressure analysis method, wherein the blood pressure analysis system described previously operates in conjunction with application software read from a computer readable medium that executes on a variety of computerized hardware that includes but is not limited to microcontrollers, personal computers, laptops, tablet computers, cellphones, smartphones, and the like.

BRIEF DESCRIPTION OF THE DRAWINGS

For a fuller understanding of the advantages provided by the invention, reference should be made to the following detailed description together with the accompanying drawings wherein.

DESCRIPTION OF THE PRESENTLY PREFERRED EXEMPLARY EMBODIMENTS

Figure 1:
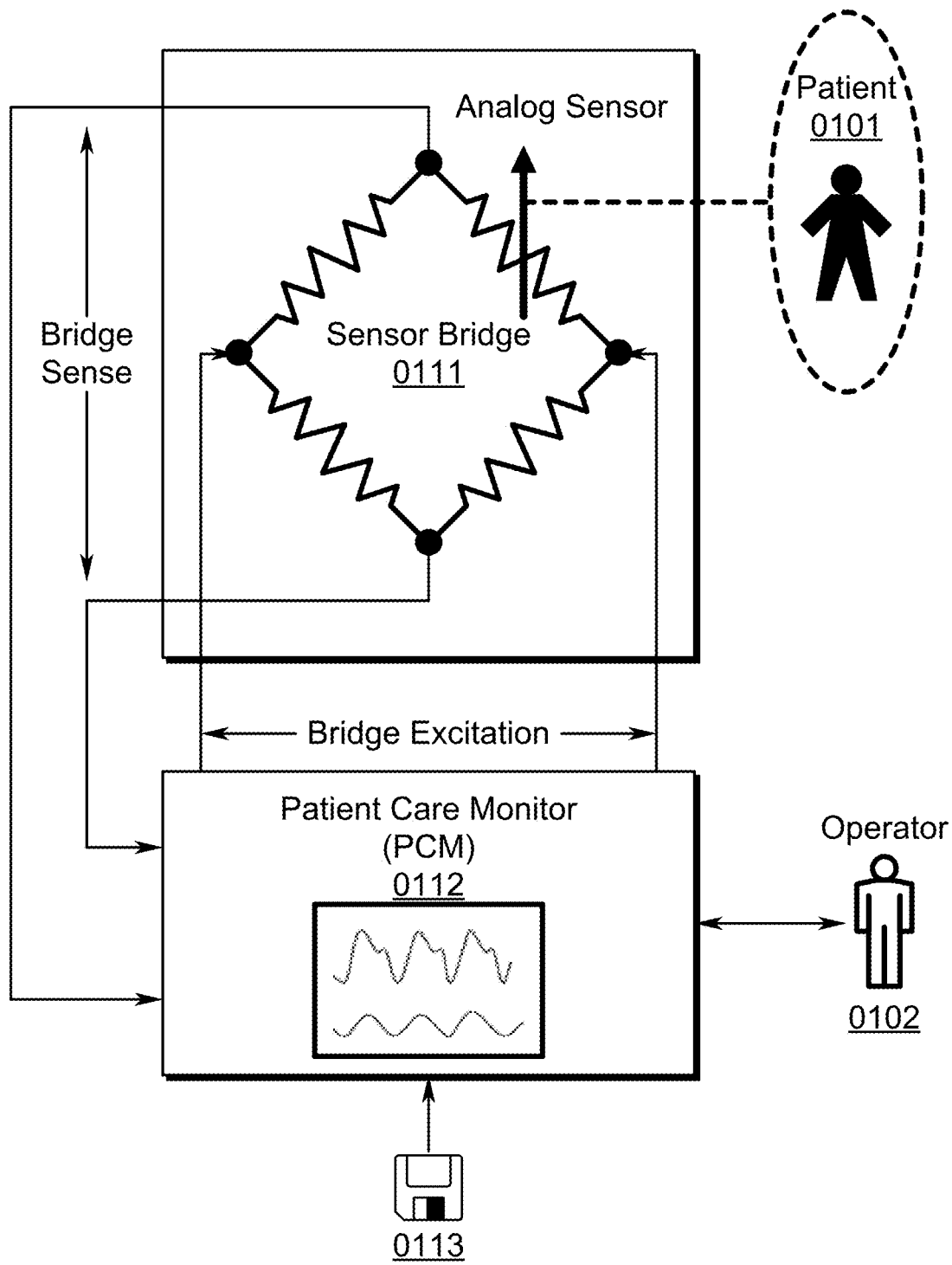
FIG. 1 illustrates a system block diagram of a prior art blood pressure analysis system as applied to an analog patient status sensor monitored by a patient care monitor (PCM)
Figure 2:
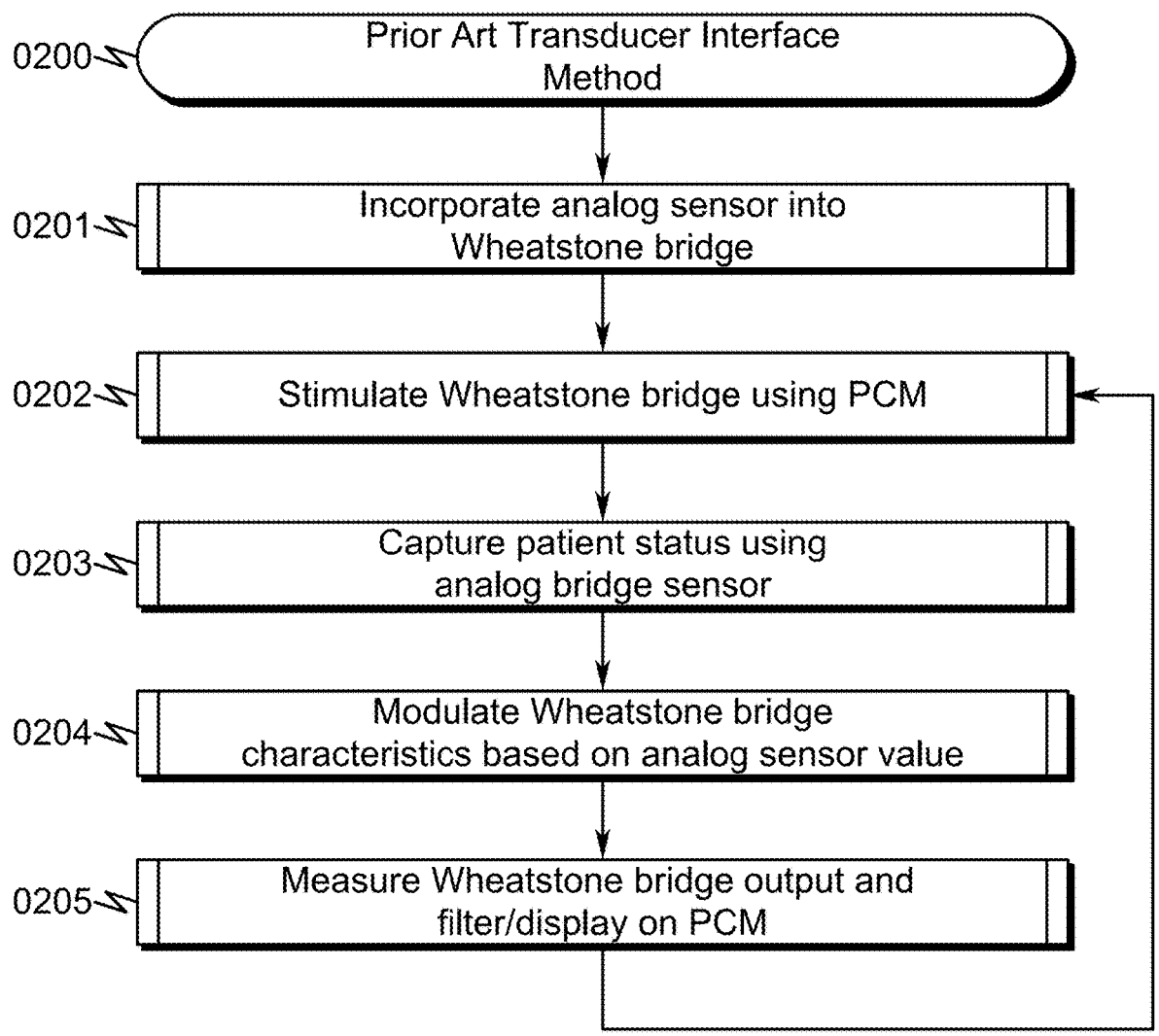
FIG. 2 illustrates a method flowchart of a prior art blood pressure analysis method as applied to an analog patient status sensor monitored by a patient care monitor (PCM)

While the present invention is susceptible of embodiment in many different forms, there is shown in the drawings and will herein be described in detailed preferred embodiment of the invention with the understanding that the present disclosure is to be considered as an exemplification of the principles of the invention and is not intended to limit the broad aspect of the invention to the embodiment illustrated.

The numerous innovative teachings of the present application will be described with particular reference to the presently preferred embodiment, wherein these innovative teachings are advantageously applied to the particular problems of a BLOOD PRESSURE ANALYSIS SYSTEM AND METHOD. However, it should be understood that this embodiment is only one example of the many advantageous uses of the innovative teachings herein. In general, statements made in the specification of the present application do not necessarily limit any of the various claimed inventions. Moreover, some statements may apply to some inventive features but not to others.

BPM not Limitive

Much of the discussion of the present invention will center on a blood pressure monitoring (BPM) system embodiment. However, the teachings of the present invention are not strictly limited to the measurement of blood pressure. Thus, while the term "BPM" is used to identify the present invention in a variety of embodiments, it does not limit the invention to blood pressure measurement.

Analog Sensor not Limitive

Within the context of the present invention, the term "analog sensor" should be broadly construed to include sensors having analog and/or digital interfaces.

Fiber Optic Sensor not Limitive

The present invention anticipates a wide variety of fiber optic pressure sensors may be incorporated in various invention embodiments, including but not limited to fiber optic sensors utilizing an interferometer and/or ratiometric measurement techniques.

Computing Device not Limitive

The present invention may utilize a wide variety of computing devices in various embodiments described herein. However, the present invention is not specifically limited to implementation with a given type of computing device. Therefore, terms such as "computer," "microcontroller," "MCU," "digital signal processor," "DSP," "laptop," "smartphone," "tablet computer," and the like should be considered synonymous in this context and given their widest possible interpretation consistent with the remaining teachings of the present invention.

Blood Pressure Sensor not Limitive

Within the context of the present invention, the term "blood pressure sensor" should be broadly construed to include any sensor that measures pressure, whether applied to blood pressure monitoring or some other type of pressure sensor monitoring.

Pulse Rate not Limitive

Within the context of the present invention description, the terms "heart rate," "pulse rate," and the like are synonymous.

Computer not Limitive

The present invention anticipates a wide variety of computing devices may be used to implement the various aspects of the present invention and makes no limitation on the type of computing device that may be used to implement these functions. Thus, the term "computer," "computing device" and their derivatives should be given the broadest possible definition in this context.

Patient Care Monitor (PCM) not Limitive

Within the present invention description the terms "Patient Care Monitor," "Patient Monitor," and "PCM" are synonymous. Furthermore, these terms should be given their broadest possible meaning in that PCM systems may include a wide variety of digital and/or analog systems used to monitor patient conditions and provide diagnostic information used within the healthcare environment.

Replication not Limitive

The present invention may in some preferred embodiments implement multiple pressure sensing channels and/or analysis functions. Within this context, the term "replication" shall also include the use of multiplexing, wherein multiple pressure sensor inputs are multiplexed into a single pressure sensor measurement system.

Computer Communication not Limitive

The present invention anticipates the use of computer communication between a given BPM system and another computer system. This communication may also permit BPM-to-BPM communication for the purposes of supporting multiple BPM measurement systems and multi-way interoperability between a plethora of BPM systems configured to operate cooperatively. Cooperative sharing of data, and processing and storage resources in these configurations allows the ability to combine not only multiple sensors, but also to aggregate data analysis to provide a more timely and comprehensive evaluation of pressure data than could be presented using only data and resources from only a single BPM.

Typical System Context

Overview

The present invention in a preferred embodiment is an electronic interface device that provides compatibility between one or more physiological fiber optic sensors (transducers) and conventional invasive arterial blood pressure (IBP) inputs to a common physiological patient care monitor (PCM). Various invention embodiments integrate the output from a signal conditioner, that itself receives inputs from a fiber optic sensor apparatus, with the output from a physiological monitor originally designed to interface with an external pressure transducer and generates an input to that monitor consisting of an accurate replication of the inputs that would be received from a Wheatstone Bridge external pressure transducer. The signal conditioner may be defined as an electro-optical unit that controls, processes, and converts the pressure modulated light signal from the transducer into electrical signals for subsequent interpretation. The present invention converts the optical sensor data to electrical signals that may then be interpreted by a conventional patient care monitor (PCM) and/or is retained and displayed directly on the device. The embodiment accurately emulates a fluidic IBP transducer and supplies electrical signals to its output that are indistinguishable from a conventional fluidic blood pressure sensor. It also supports modern computer communications interfaces and analog/digital human interface status indicators. Various preferred invention embodiments are designed to be used primarily in surgical procedures and critical patient care situations where the accuracy and timeliness of IBP systolic and diastolic measurements are very important. The present invention explicitly supports disposable fiber optic sensors that may be incorporated into other medical devices such as catheters and sheaths.

Fiber Optic Pressure Transducers

Modern fiber optic pressure transducers are less than 500 microns in diameter and are constructed using micro-machining manufacturing techniques. These tiny silicon-glass transducers are attached to the distal end of a standard fiber optic cable and are surgically placed into a human or animal body for IBP sensing. The proximal end of the sensor cable (which can be arbitrarily long) is attached through a fiber optic connector to an electro-optical signal conditioner unit that controls, processes and converts the pressure modulated light signal from the transducer into electrical signals for subsequent interpretation. Although fiber optic transducer systems have been used for blood pressure measurement as laboratory instruments, they have incompatible electrical output connections that do not allow them to be attached to conventional patient care monitors (PCMs). This limitation has kept these devices from gaining widespread use. The present invention in some preferred embodiments creates the sensor-to-monitor compatibility as well as providing expanded functionality for enhanced applications such as real time analysis of IBP waveforms and dynamic control of data acquisition and display.

PCM Interface

Figure 3:
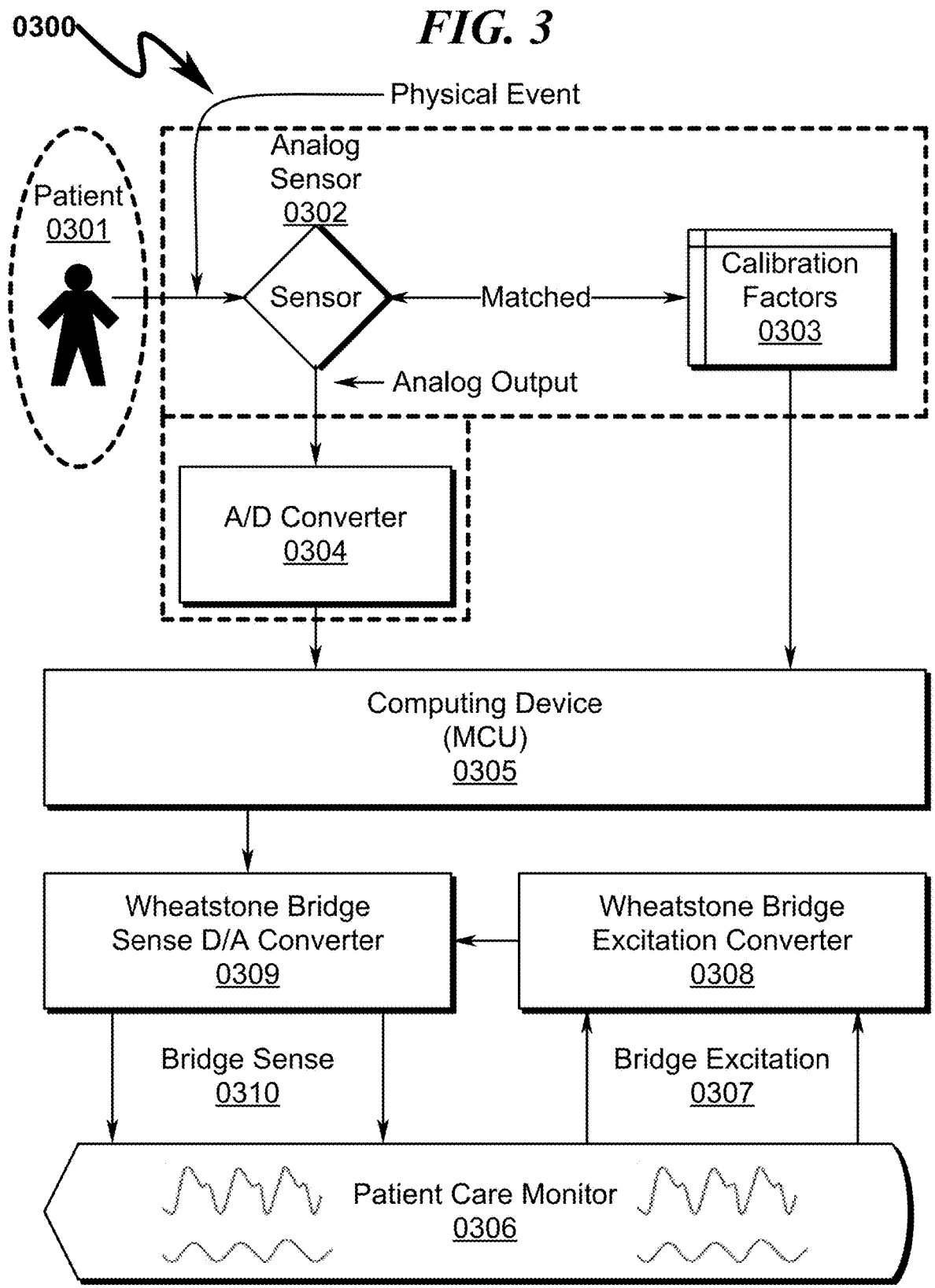
FIG. 3 illustrates a system block diagram of a preferred exemplary system embodiment of the present invention blood pressure analysis system as applied to an analog patient status sensor monitored by a patient care monitor (PCM)

The present invention may be implemented as a self-contained unit that has a fiber optic transducer connection as an input source and communicates with a patient care monitor (PCM) as its output as generally depicted in FIG. 3 (0300). The interface essentially acts to directly emulate the electrical interface characteristics of conventional fluidic pressure transducers (that common patient care monitors (PCMs) are compatible with) while providing much more accurate blood pressure data derived from a fiber optic sensor. Electrically emulating a conventional fluidic transducer uniquely allows a fiber optic pressure sensor to be used with a wide variety of existing physiological patient care monitors (PCMs) without modification of those monitors.

BPM Exemplary Application

Fiber optic pressure sensors are extremely accurate and when placed in an arterial blood vessel provide significantly better real time blood pressure information to a clinician. Specifically, medical personnel such as cardiologists, vascular surgeons, anesthesiologists, neurosurgeons, interventional radiologists, trauma physicians, emergency medical technicians, etc. all need accurate real time indications of a patient's arterial blood pressure during critical care situations. Fiber optic sensors are also immune to the effects of electromagnetic radiation and can be used in intense radiological imaging environments without degradation, thus providing the ability to provide superior real time measurements in many clinical settings.

Basic Theory of Operation

A conventional fluidic IBP sensor uses a Wheatstone Bridge circuit (or a variant thereof) where the legs of the bridge circuit incorporate resistive or strain gauge elements as generally depicted in FIG. 1 (0100). An excitation voltage is applied by a conventional IBP monitor to the input of the bridge to provide an energizing voltage and a reference for the output signal. When pressure is applied to the sensor(s) the bridge becomes unbalanced and creates a small analog signal that is directly proportional to the pressure activated change in the sensor resistance. The most common sensitivity value for these sensors is 5-microvolts/volt/mmHg. Although the sensitivity value is reasonably standard in the industry various manufacturers of patient care monitors (PCMs) use a variety of excitation voltages.

The present invention has an adaptive Wheatstone Bridge emulation function as generally depicted in FIG. 3 (0300) that senses the instantaneous excitation voltage from the patient care monitor (PCM) to which it is connected. It then automatically applies corrections to the absolute fiber optic pressure sensor signal to scale it to the appropriate values needed by the specific patient care monitor (PCM).

The present invention incorporates optional user human interfaces that provide information and control functions. Among these functions are:

an electronic display capable of showing systolic blood pressure, diastolic blood pressure, mean blood pressure, and/or heart rate values and system status, light indicators showing system condition and alarms, an audio alarm annunciator, and manual switch controls for turning the unit on and off, audio muting, etc.; and an automatic zeroing function to atmospheric pressure when the sensor is connected to the signal conditioner prior to the insertion of the device into a body cavity of a patient.

These display and control functions are also available through a computer communications port for software application control.

The present invention may be powered selectively by either batteries or by a standard AC utility outlet. The battery can be either primary cells or rechargeable batteries.

System Overview (0300)

The present invention system may be seen in an overview context as generally illustrated in FIG. 3 (0300), wherein the system is applied to collection of data associated with a patient in a healthcare application context. Within this context, the patient (0301) is monitored by an analog sensor (0302) that has associated with it calibration factors (0303) that describe a conversion from the analog values produced by the sensor (0302) to a normalized set of standardized values. For example, a fiber optic pressure sensor might incorporate calibration factors converting measured optical transit delays (or other measured physical data associated with the optical sensor) to absolute pressure values.

The analog sensor (0302) analog output is converted to digital by an A/D converter (0304) and this information with the calibration factors (0303) is presented to a microcontroller (MCU) (0305) (or other computing device) for integration. In this step the raw analog sensor (0302) information is compensated by the calibration factors (0303) to produce sensor data that may be interpolated if necessary to produce accurate sensor information that is accurate over a wide dynamic range of sensor inputs.

Within this general system context in many preferred configurations a patient care monitor (PCM) (0306) generates analog excitation signaling (0307) that is used as a scaling reference for the Wheatstone Bridge Excitation Converter (0308). The analog sensor A/D converter data and the calibration factor data are combined to produce a Wheatstone Bridge sense output that is converted by a D/A converter (0309) for combination with the excitation signaling data and subsequent presentation to the PCM (0306) as an analog bridge sense signal (0310). This analog bridge sense signal (0310) represents a fully compensated and calibrated conversion of the analog sensor (0302) output that is scaled in proper form for processing and display by the PCM (0306).

Method Overview (0400)

Figure 4:
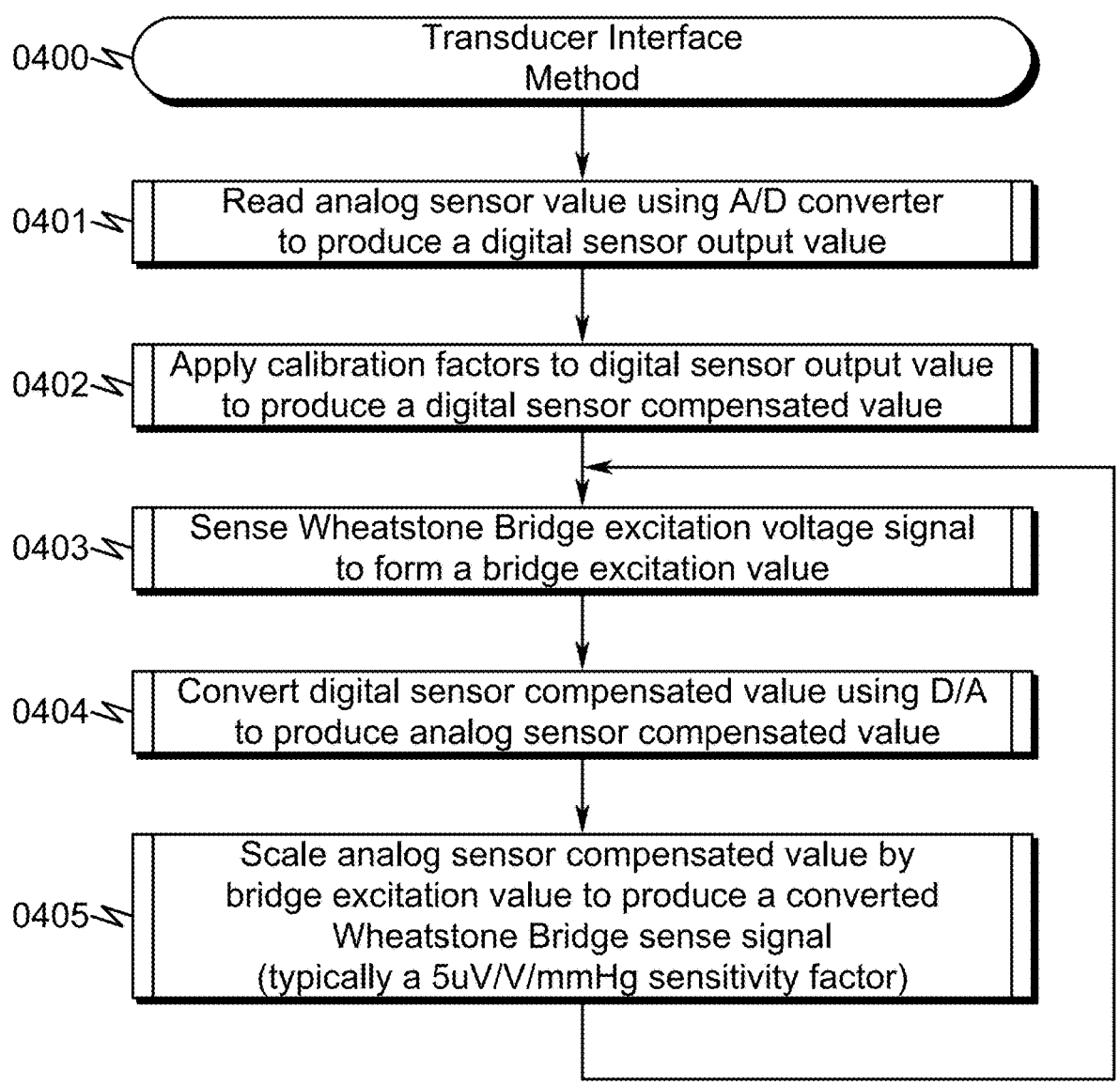
FIG. 4 illustrates a method flowchart of a preferred exemplary method embodiment of the present invention blood pressure analysis method as applied to an analog patient status sensor monitored by a patient care monitor (PCM)

The present invention method may be seen in an overview context as generally illustrated in the flowchart of FIG. 4 (0400), and can be generally described as a blood pressure analysis method that comprises the following method steps:

(1) Sampling an analog sensor output signal using an A/D converter to produce a digital sensor output value (0401);

(2) Applying calibration factors to the digital sensor output value to produce a digital sensor compensated value (0402);

(3) Sensing a Wheatstone Bridge excitation voltage signal to form a bridge excitation reference voltage (0403);

(4) Converting the digital sensor compensated value from digital to analog using an A/D converter to produce an analog sensor compensated value (0404); and (5) Scaling the analog sensor compensated value by the bridge excitation value to produce a converted Wheatstone Bridge sense signal (0405).

One skilled in the art will recognize that these method steps may be augmented or rearranged without limiting the teachings of the present invention.

System Block Diagram Description (0500, 0600)

Figure 5:
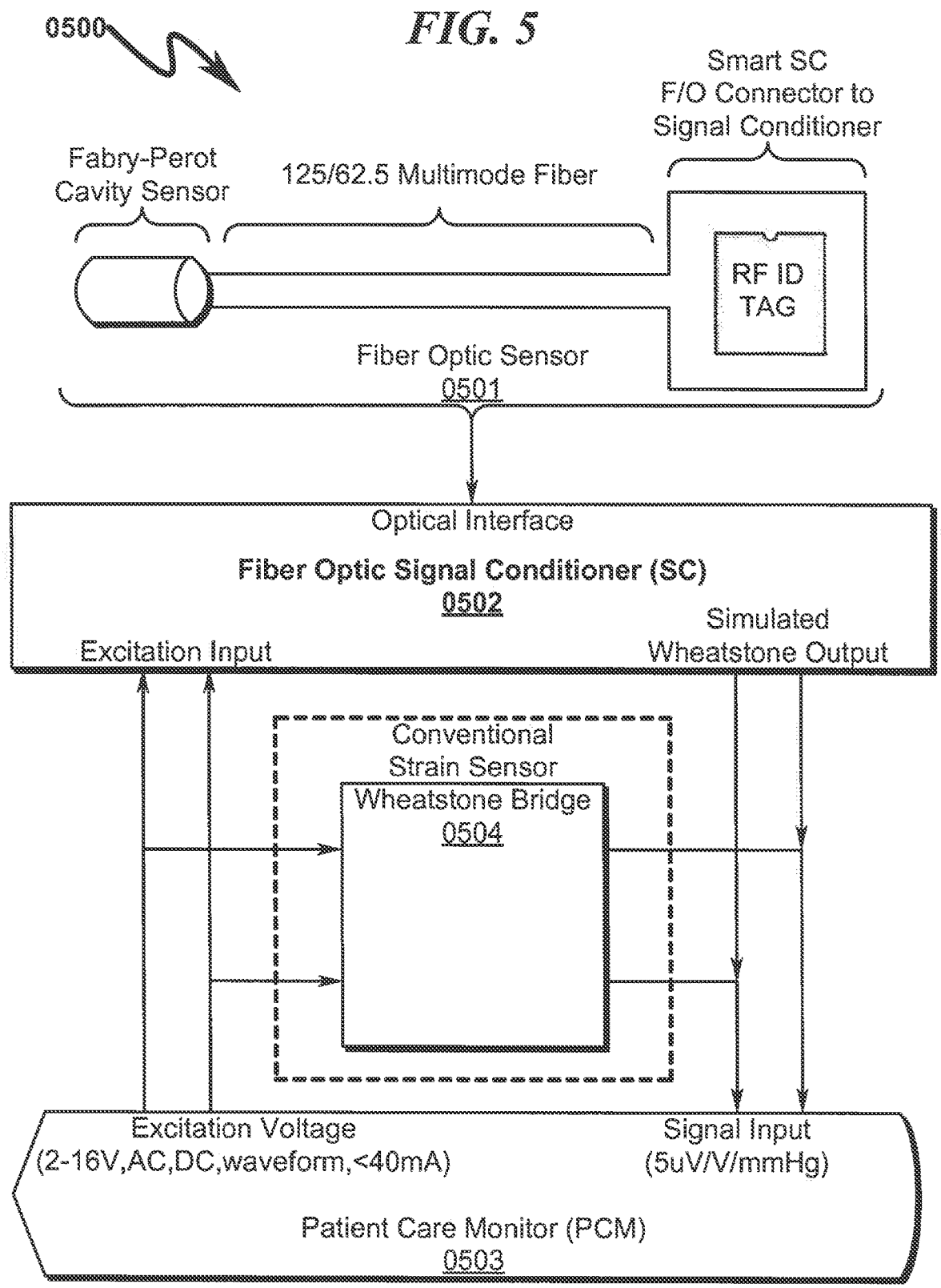
FIG. 5 illustrates an exemplary PCM interface embodiment utilizing teachings of the present invention.

FIG. 5 (0500) depicts the basic components of a blood pressure monitoring system which the present invention makes compatible with conventional PCMs.

FIG. 5 (0500) schematically shows the basic components of a fiber optic pressure sensor assembly (0501). It consists primarily of three parts. One part is a Fabry-Perot (F-P) pressure sensitive diaphragm mounted at the distal end of a cavity which is the transducer itself. Pressure induced deflections of this diaphragm modulate light shining on it and reflect the light down the fiber optic cable which is the second part. The third part is a fiber optic connector that connects to a signal conditioner (0502) and contains a non-volatile memory holding sensor specific gauge factors.

The Fiber Optic Signal Conditioner (0502) detailed in FIG. 5 (0500) represents a schematic block diagram of one instantiation of an electro-optic signal conditioning device that excites a fiber optic Fabry-Perot pressure sensor and processes the reflected light into an electrical signal proportional to the physiological pressure on the sensor. The optical interferometer combines the excitation light and the reflected signal light to produce an optically modulated signal that indicates the pressure-induced deformation of the F-P sensor cavity. This optically modulated signal is detected using photodetectors (or alternatively detected by a CCD imaging array) and converted to an electrical signal that is stored in a digital memory used for subsequent processing. The microprocessor processes the digital pressure data and converts it to a format compatible with a serial digital output and/or supplies the data to a digital-to-analog converter that produces an analog signal output. A power electronics subsystem (not shown) converts a single power input into multiple voltages needed by the various components in the signal conditioner.

The bottom of FIG. 5 (0500) shows the main parts of a conventional IBP patient care monitor (PCM) (0503) and a Wheatstone Bridge resistive pressure sensor (0504). The bridge is excited by a voltage from the patient care monitor (PCM) as shown. The sensor elements change their resistances based on the strain (pressure) on them. These changes in the resistance values unbalance the bridge and produce a voltage proportional to the excitation voltage and the pressure. The fiber optic signal conditioner (0502) substitutes the fiber optic sensor (0501) for the conventional strain sensor (0504) used by the PCM (0503).

Figure 6:
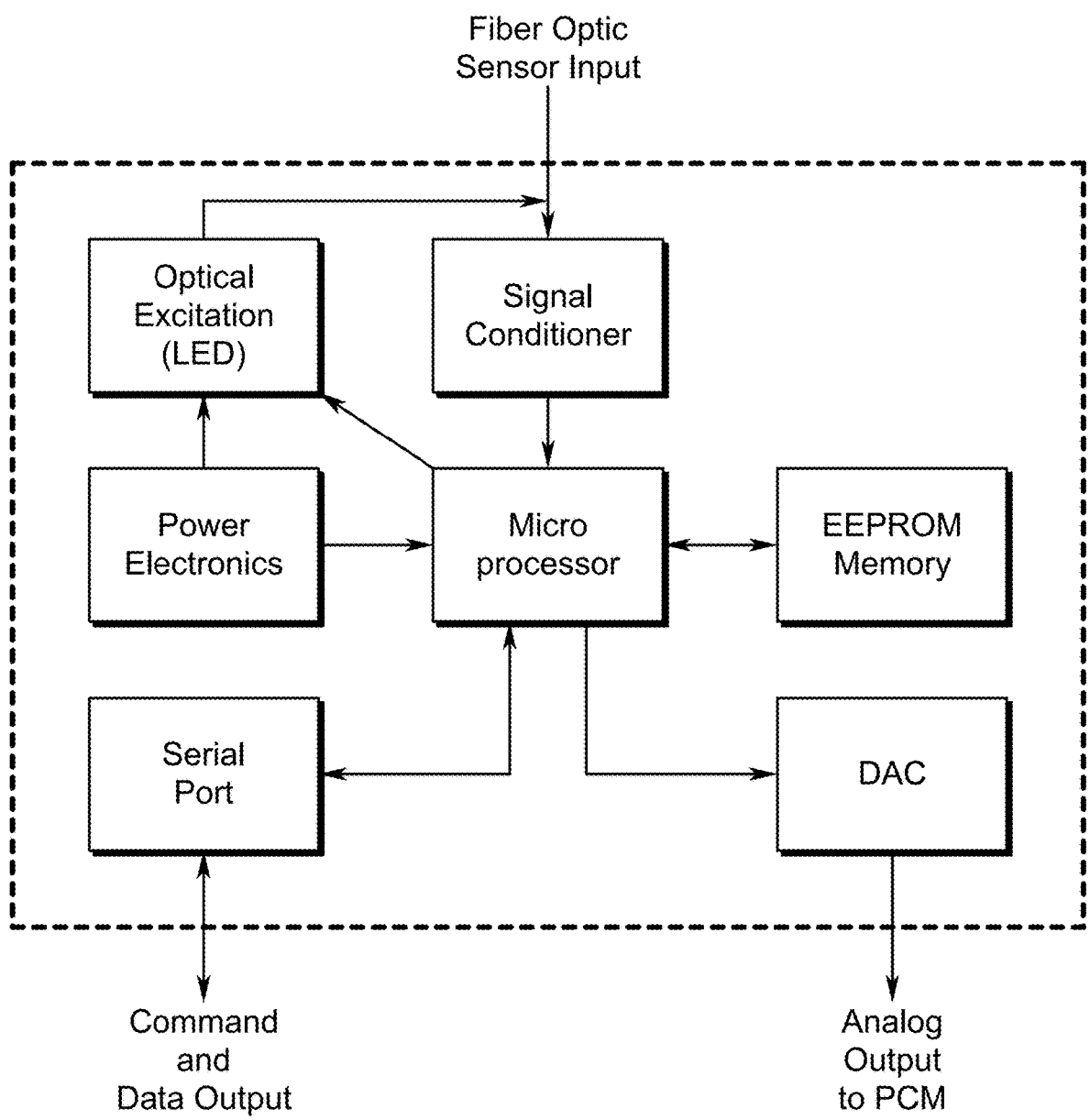
FIG. 6 illustrates exemplary internal logic interface detail of a present invention embodiment that interfaces between a fiber optic pressure sensor, a PCM, and an auxiliary command/data processor.

FIG. 6 (0600) depicts a schematic block diagram of the major components of the present invention including the signal conditioner (0502) previously shown in FIG. 5 (0500) and the conventional patient care monitor (PCM) shown earlier in FIG. 5 (0500). However the Wheatstone Bridge is now replaced by a connection to the fiber optic interface.

Major functions and internal architecture of the present invention (interface) are schematically shown in the large central block. One or more of the outputs of the fiber optic signal conditioner is connected to the interface electronically. Both commands and pressure data travel over the digital connection, where only the pressure information is present on the analog connection. If needed this analog signal is converted to a digital signal by an analog-to-digital converter (ADC) and stored in random access memory (RAM) by the microprocessor for subsequent processing. The digital communications interface block converts the data using the appropriate communications protocol and the data is stored in RAM memory.

The microprocessor is the central processing element in the system and provides the ability to support many other functions than just processing blood pressure data. The microprocessor executes instructions stored in the firmware EEPROM that manage and process functions such as diagnostics, error handling, normal operation, alarms, etc. The input communications interface sends control commands to the fiber optic signal conditioner as directed by the microprocessor. Another major task of the microprocessor is to control the function of emulating a conventional non-fiber optic pressure sensor. This is accomplished through continuously reading the particular IBP excitation voltage present at the patient care monitor (PCM) and conditioning the pressure data to be proportional to it as the monitor expects. The microprocessor processes the data stream and sends it to a digital-to-analog converter (DAC) after which it is scaled to the appropriate values for direct output to the patient care monitor (PCM). During this conversion the microprocessor applies a previously selected sensitivity factor (typically either 5-microvolts/volt/mmHg or 40-microvolts/volt/mmHg)) appropriate to the patient care monitor (PCM) that is connected to the interface monitor output. This emulation ability provides compatibility with conventional patient care monitors (PCMs).

The firmware EEPROM is externally accessible through a second digital communications interface by other computer applications for updating the firmware. This second digital communications interface supports multiple communications protocols. The microprocessor also manages the human interface devices local to the interface. These devices may comprise switches, visual and/or aural indicators, and/or an alphanumeric blood pressure display.

As detailed in subsequent FIGURES, this pressure measurement interface may be powered by either a battery or by a power adapter that converts utility AC power to a DC voltage for the interface. An internal power converted breaks down the main DC power source into multiple DC power voltages used by various components in the interface.

Intelligent Patient Monitor Interface (0700, 0800)

Figure 7:
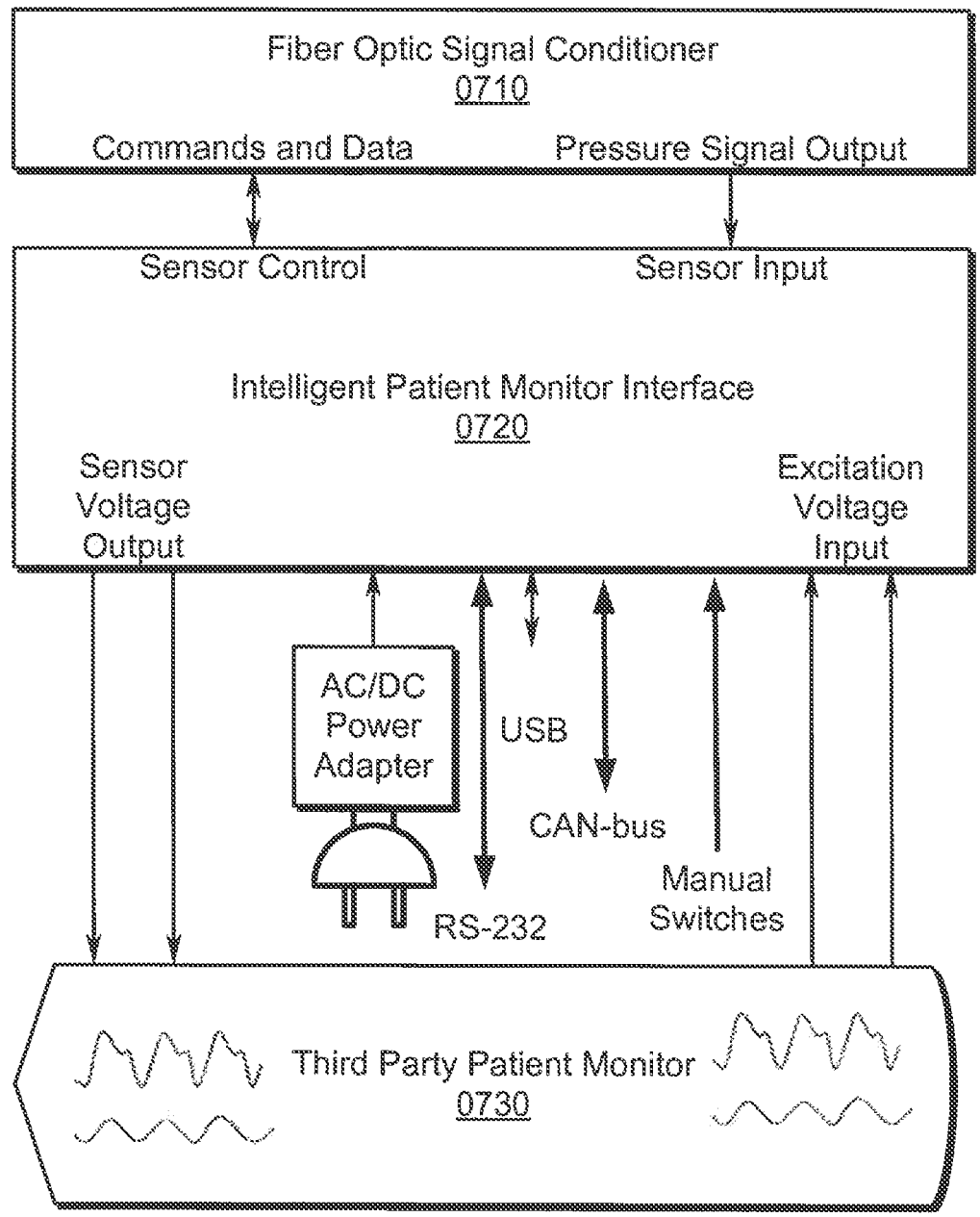
FIG. 7 illustrates a preferred exemplary embodiment of the present invention as applied to an intelligent patient care monitor (PCM) interface.

A preferred embodiment of the present invention applied to a generic pressure sensing application is depicted in FIG. 7 (0700), wherein a fiber optic signal conditioner (0710) interfaces with a fiber optic pressure sensor to generate output signaling based on measured pressure in response to commands and/or data received from an intelligent patient monitor interface (IPMI) (0720). The IPMI acts as the "bridge" between the fiber optic pressure signal conditioner (0710) and a third party patient care monitor (PCM) (0730) configured to accept Wheatstone Bridge compatible pressure sensors. Within this context excitation voltages generated by the PCM (0730) are used by the IPMI (0720) to scale/reference the sensor voltage outputs used to driver the Wheatstone Bridge inputs of the PCM (0730).

Figure 8:
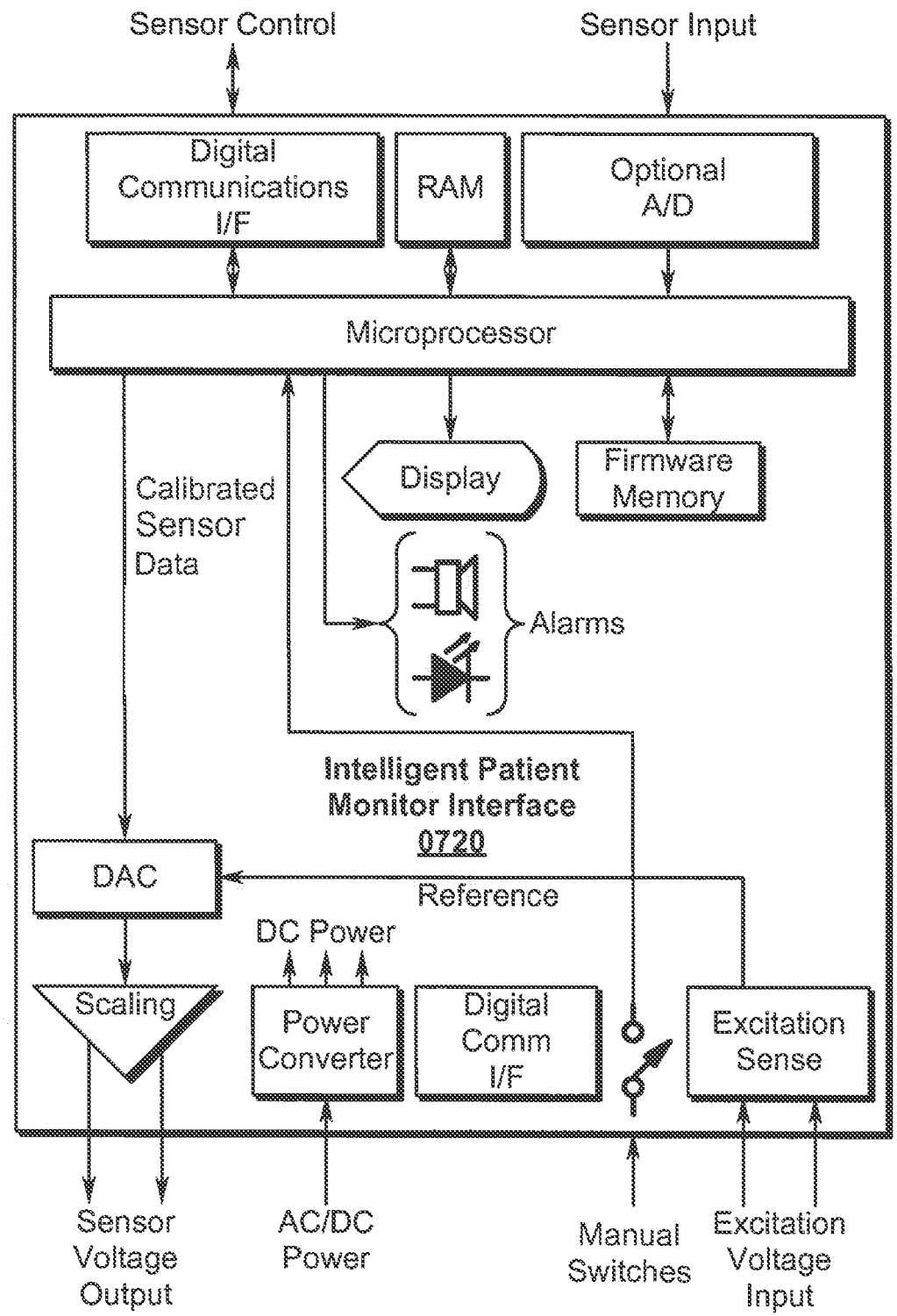
FIG. 8 illustrates a preferred exemplary embodiment of the present invention as detailing the internals of an intelligent patient care monitor (PCM) interface.

More detail of the IPMI in this context can be observed in FIG. 8 (0800) wherein the internals of the IPMI (0720)

generally comprise a microprocessor, RAM, digital communications interfaces, optional A/D converter, display, firmware program memory, human interface alarms, excitation sensing and sensor output voltage generation circuitry, as well as power conversion circuitry and provisions for digital communication to other processors.

Pressure Selection/Analysis/Sampling and Display (0900)

Conventional Blood Pressure Display

Figure 9:
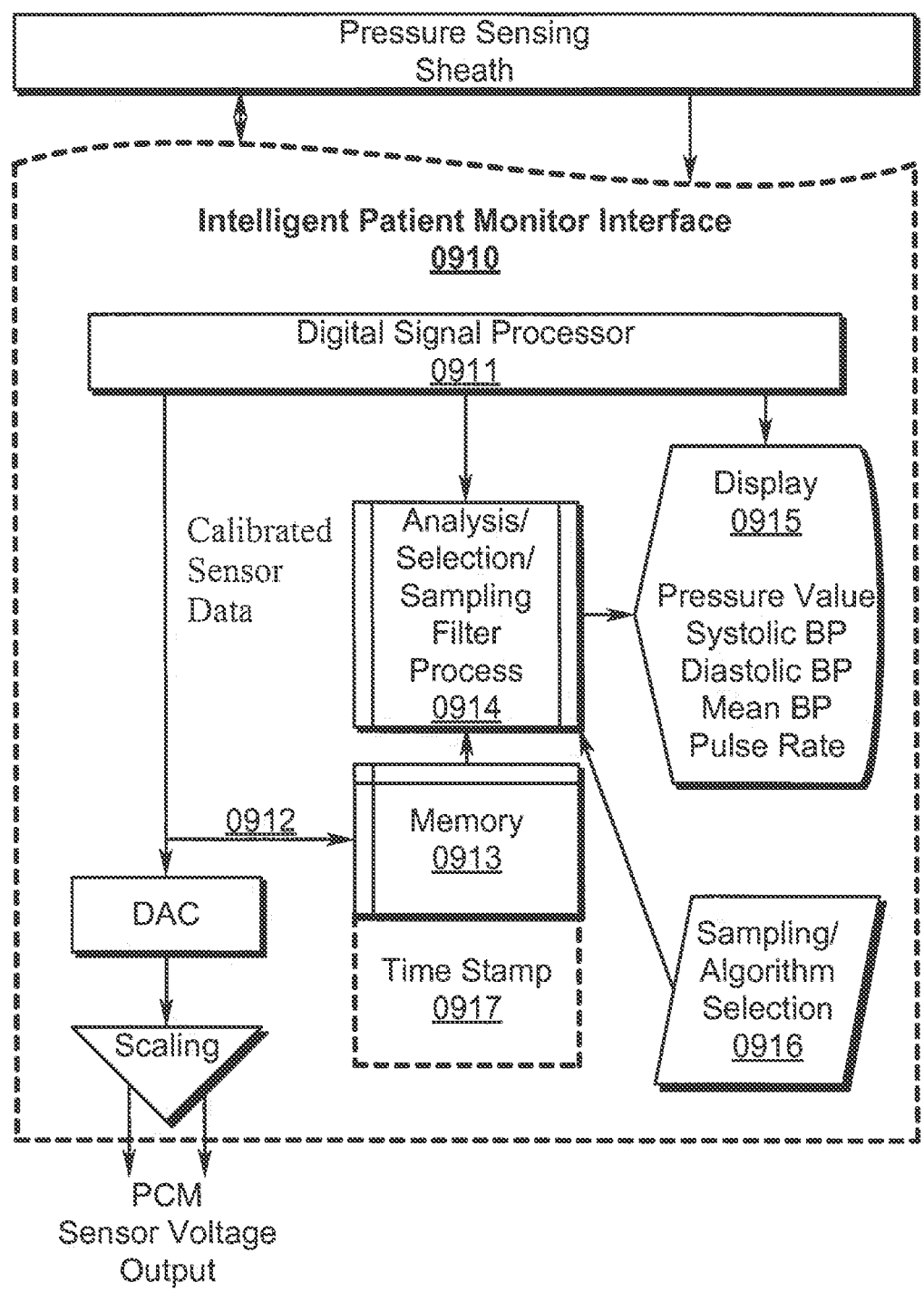
FIG. 9 illustrates a preferred exemplary embodiment of the present invention as applied to an intelligent patient monitoring interface in the context of a conventional blood pressure monitor (BPM) system configured to display systolic blood pressure, diastolic blood pressure, mean blood pressure, and heart rate values; implementing memory storage of pressure data and selection of this pressure data for presentation on a display; implementing memory storage of pressure data and analysis of this pressure data for presentation on a display; implementing memory storage of pressure data and sampling of this pressure data for presentation on a display.

As generally illustrated in FIG. 9 (0900), the present invention anticipates an embodiment wherein the intelligent patient monitor interface (0910) permits the calibrated sensor data (digital bridge sense value computed by the digital signal processor (0911)) (0912) to be displayed (0915) as a systolic blood pressure, diastolic blood pressure, mean blood pressure, and/or heart rate value.

Selected Pressure Display

As generally illustrated in FIG. 9 (0900), the present invention anticipates an embodiment wherein the intelligent patient monitor interface (0910) permits a plethora of calibrated sensor data (digital bridge sense value computed by the digital signal processor (0911)) (0912) to be stored in a memory device (0913) and processed by a selection process (0914) (typically under control of the digital signal processor (0911)) and then presented on a visual display device (0915). The selection process (0914) may optionally incorporate a human interface to permit definition of the selection criterion (0916).

One skilled in the art will recognize that a wide variety of selection methodologies may be implemented in the selection process (0914), including but not limited to mean, peak, weighted averaging, and other methodologies.

Analyzed Pressure Display

As generally illustrated in FIG. 9 (0900), the present invention anticipates an embodiment wherein the intelligent patient monitor interface (0910) permits a plethora of calibrated sensor data (digital bridge sense value computed by the digital signal processor (0911)) (0912) to be stored in a memory device (0913) and processed by an analysis process (0914) (typically under control of the digital signal processor (0911)) and then presented on a visual display device (0915). The analysis process (0914) may optionally incorporate a human interface to permit selection of the analysis algorithms (0916) to be applied to the pressure data (0912).

One skilled in the art will recognize that a wide variety of signal analysis methodologies may be implemented in the analysis process (0914), including but not limited to averaging, curve fitting, interpolation, extrapolation, peak fitting, peak selection, mean averaging, and other known analysis techniques. It is specifically anticipated that the high fidelity nature of the digital data (0912) will permit real-time analysis of the pressure waveforms recorded within the memory device (0913).

Sampled Pressure Display

As generally illustrated in FIG. 9 (0900), the present invention anticipates an embodiment wherein the intelligent patient monitor interface (0910) permits a plethora of calibrated sensor data (digital bridge sense value computed by the digital signal processor (0911)) (0912) to be stored in a memory device (0913) and processed by a sampling process (0914) (typically under control of the digital signal processor (0911)) and then presented on a visual display device (0915). The sampling process (0914) may optionally incorporate a human interface to permit selection of the sampling criterion (0916) to be applied to the pressure data (0912).

Note in this embodiment variant a timer and/or time stamp data (0917) may be utilized in conjunction with the memory data (0913) to select or sample a portion of a collected data sample within a given sampling period. One skilled in the art will recognize that this timing function may also be integrated within the digital signal processor (0911).

One skilled in the art will recognize that a wide variety of signal sampling methodologies may be implemented in the sampling process (0914), including but not limited to averaging, decimation, value limiting, noise filtering, and other known sampling techniques.

Hybrid Display Architectures

The data reduction, selection, analysis, and sampling techniques generally illustrated in FIG. 9 (0900) may be combined to form hybrid display architectures that integrate these techniques in a wide variety of ways. One skilled in the art will be aware from the teachings of these FIGURES and the remaining invention disclosure that these combinations present a very wide variety of possible patient monitoring capabilities.

Display Technologies

While a wide variety of displays may be utilized in the context of the present invention, the use of graphical touch screens may be optimal in many preferred embodiments. Additionally, the use of wireless links to smartphones, computer tablets, and other computing devices is also anticipated within the scope of the present invention.

Bidirectional Data Communication/Control (1000, 1100)

Communication Interfaces

Figure 10:
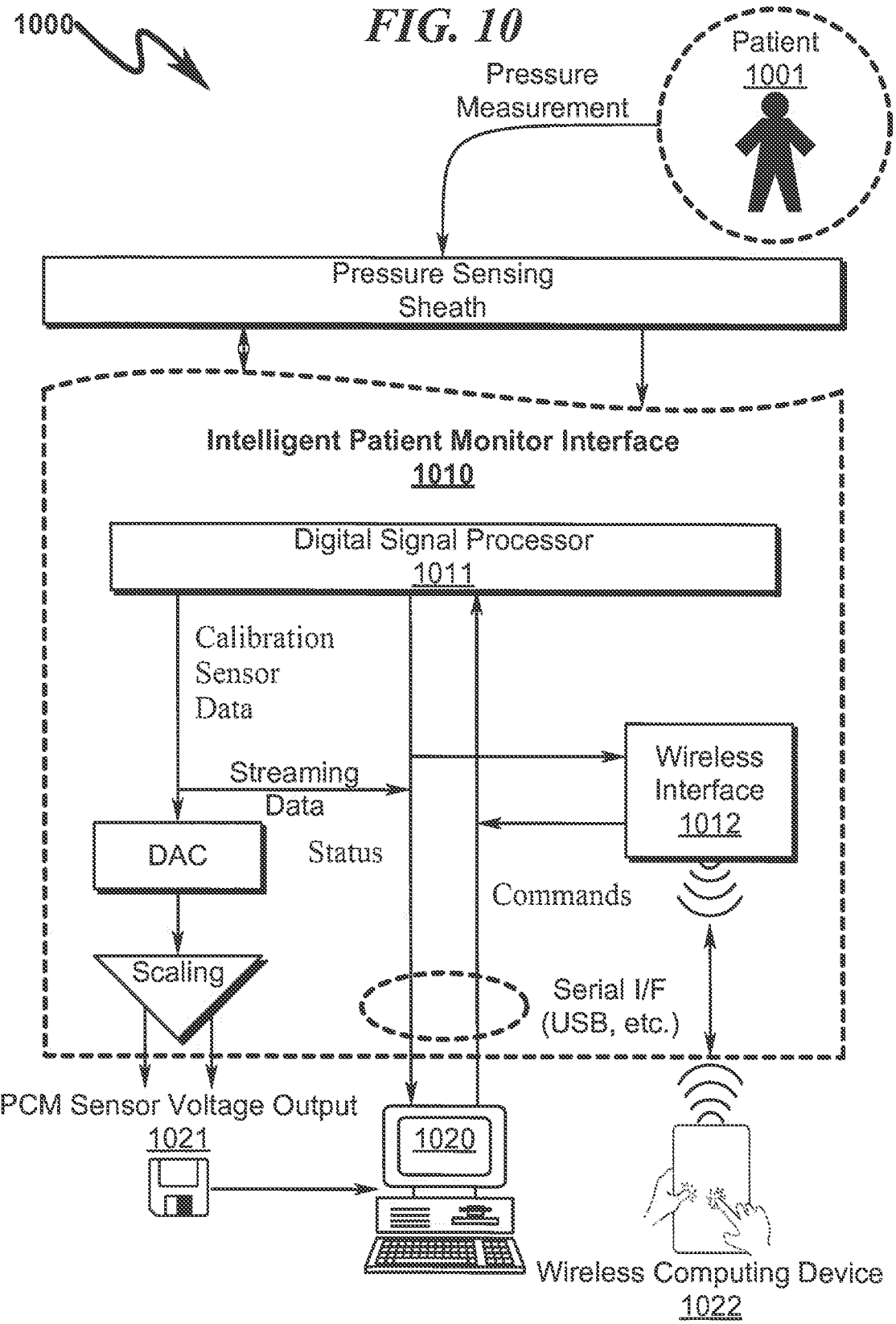
FIG. 10 illustrates a preferred exemplary embodiment of the present invention as applied to an intelligent patient monitoring interface that implements bidirectional communication with an external analysis computer using wired and wireless technologies.

As generally depicted in FIG. 10 (1000), the present invention anticipates that the digital signal processor (1011) may communicate bidirectionally with an external data analysis computer (1020) running under control of software read from a computer readable medium (1021) for the purposes of real-time/offline data/status collection by the analysis computer (1020) and/or configuration/control of the intelligent patient monitoring interface (1010) by the analysis computer (1020).

Figure 11:
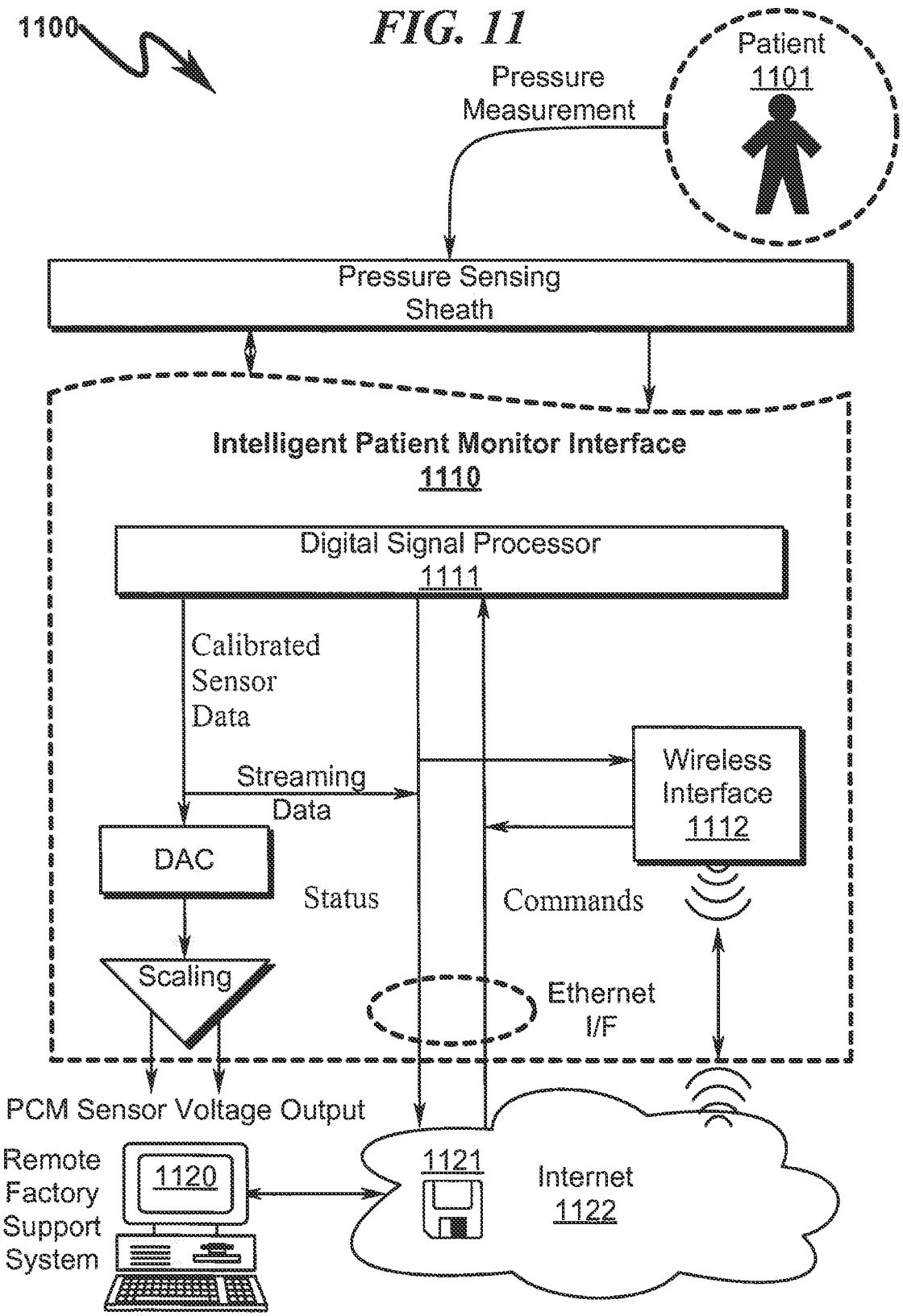
FIG. 11 illustrates a preferred exemplary embodiment of the present invention as applied to an intelligent patient monitoring interface that implements bidirectional communication over a computer network for the purposes of providing remote factory support for the BPM.

Within this context it is anticipated that a wireless interface (1012, 1112) may be incorporated into the intelligent patient monitoring interface (1010, 1110) to permit the use of remote wireless computing devices (1022) (including but not limited to laptops, smartphones, tablet computers, and the like) to function in this data analysis capacity. Alternatively, as depicted in FIG. 11 (1100), access could be provided through the Internet (1122). The present invention specifically anticipates that this wireless interface may be utilized in some preferred embodiments wherein the intelligent patient monitoring interface (1010, 1110) is part of a medical device that is embedded within a patient (1001, 1101) such that pressure measurements are taken continuously (or at specified intervals) and then wirelessly transmitted to a portable display device for storage, analysis, and/or transmission to a physician for further review and diagnosis.

Analysis Software

Within this context a wide variety of application data collection analysis software (1021) is envisioned to support patient monitoring and/or diagnosis functions to be performed by either the analysis computing devices (1020, 1022) and/or the digital signal processor (1011, 11H) contained within the intelligent patient monitoring interface (1010, 1110). On-board real-time and post-processing capability within the digital signal processor (1011, 1111) is also anticipated by the present invention. This may be implemented using a high performance processor, or multiple processors. Among the potentially valuable functions of this capability include the calculation of FFTs, sorting algorithms, searching algorithms, amplitude, power, and phase spectrums, filters, correlations, windowing, triggers, thresholding, waveform analysis, wavelet processing, encryption, decryption, formatting, timers, statistical analysis, etc. One skilled in the art will recognize that this list is non-exhaustive and merely exemplary.

Display Technologies

This analysis functionality may be combined with a wide variety of display technologies as anticipated by the present invention. This may include a high resolution graphical display, optionally including touch screen technology for some applications. This display would be capable of supporting multiple types of graphical read outs (and inputs). Among the information that could be displayed are: spectral information, amplitude waveforms, filter characteristics, diagnostics, waveform analysis, etc. This capability may directly support the display of sophisticated data analysis detailed above. One skilled in the art will recognize that this list is non-exhaustive and merely exemplary. This capability enables more sophisticated user interaction and simpler user interface development and software updates using soft keys.

Logging

The analysis functions detailed above may incorporate a sophisticated internal logging function. In concert with the conventional blood pressure processing applications detailed previously, this logging function tracks and stores information such as: sensor performance, environmental exposure, functional monitoring (e.g. power cycles, optics environment, LED life, etc.), software licensing, maintenance periods, compatibility parameters, data quality control, errors, crashes, condition-based maintenance monitoring, PSS insertions and tracking, etc. One skilled in the art will recognize that this list is non-exhaustive and merely exemplary.

Factory/Field Maintenance

As generally illustrated in FIG. 10 (1000), the present invention anticipates that a serial interface (USB, etc.) may be used to communicate between the intelligent patient monitor interface (1010) and an external computer system for use as a factory maintenance connection. This maintenance functionality may also be field-based, wherein condition-based self-assessment or remote instrument diagnostics and maintenance using wired or wireless connections through the Internet (1122) are implemented as depicted in FIG. 11 (1100). This anticipated capability allows local condition-based as well as factory level diagnostic and maintenance functions (1120) to be performed remotely in the field, thus reducing costs and down time. This capability, coupled with the analysis and logging capabilities detailed above, allow the BPM to "call home" when certain conditions occur (outbound device-initiated communication) as well as be accessed by a remote person or application (inbound remotely initiated) to collect information, diagnose problems, devise solutions, download software (1121), and correct problems in the field.

Blood Pressure Analysis System Embodiments (1200)-(1600)

The present invention anticipates that the transducer interface described above can be integrated within a variety of blood pressure analysis systems/methods, including but not limited to the following variants:

Specialized BPM Systems. Specialized neonatal and trauma BPM systems designed to accurately monitor patients who have near unity systolic/diastolic BP ratios, including smart BP windowing (4 second) and detailed BP waveform analysis.

Differential BP Sensing. Probes and systems designed to permit multiple blood pressure readings over areas associated with one or more BP probes.

Streaming BP Data Analysis. Blood pressure monitoring integrated with dynamic computerized analysis of streaming data.

Wireless/Remote BP Monitor. Use of a portable wireless device (tablet, smartphone) integrated with blood pressure monitor to analyze and display monitored results. The portable device is capable of accuracy not possible with conventional PCM systems.

Customized BP Analysis. Menu selection of various medical analysis programs to be downloaded into a portable device (tablet, smartphone) for download into the blood pressure monitor to permit reconfiguration of the BPM in the field and selection of customized analysis programs for a given patient.

These specifically anticipated variations are described in more detail below.

Specialized BPM Systems (1200)

Figure 12:
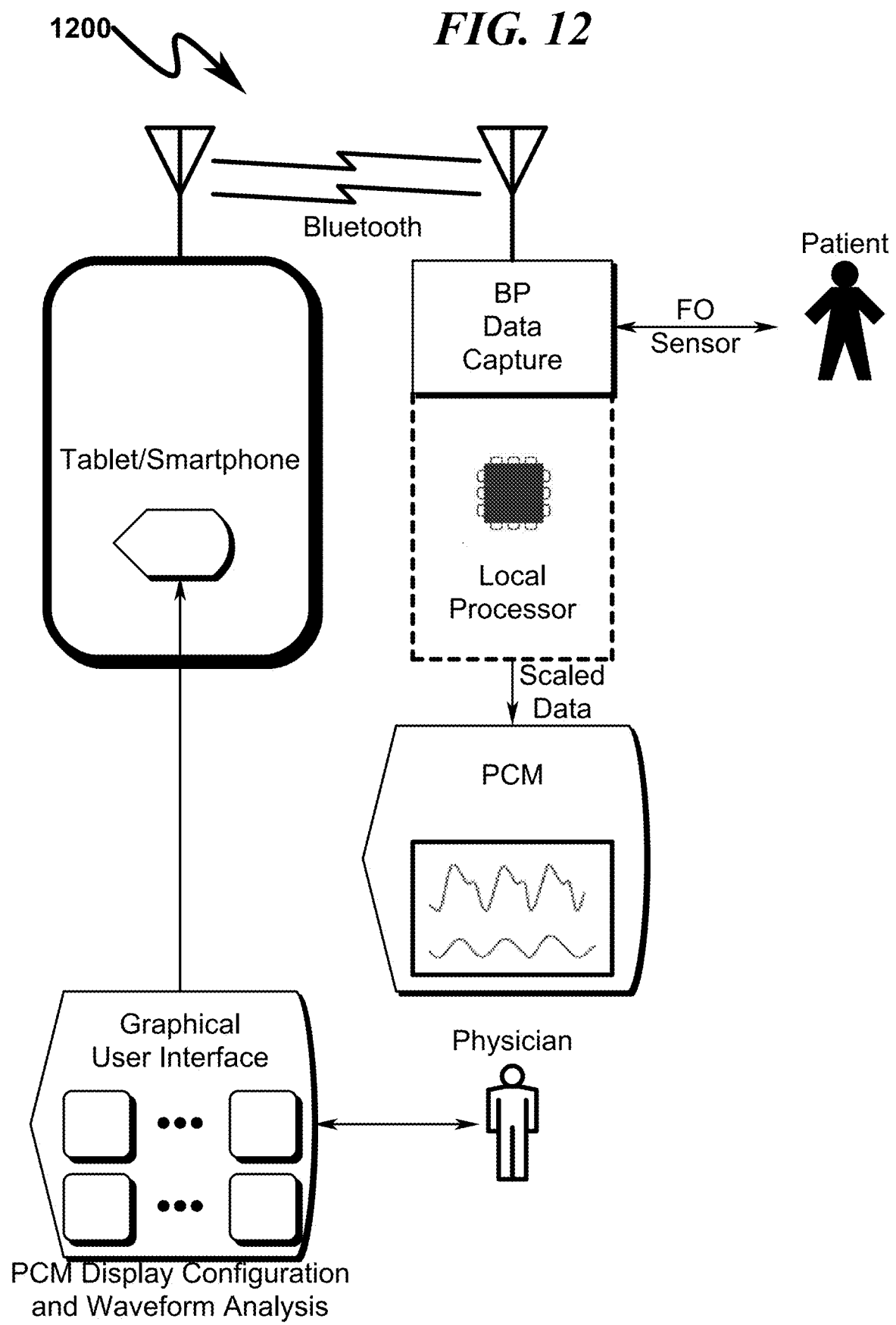
FIG. 12 illustrates an exemplary specialized BPM system architecture.

As generally depicted in FIG. 12 (1200), this variant of the BPM system capitalizes on the high data capture rate of the BP system as well as its ability to capture BP events when the systolic/diastolic pressures approach unity. This capability has targeted applications in neonatal care units as well as trauma centers where the patient vital signs are often too weak to be accurately captured by conventional PCM systems. In this scenario two options are available. In the first, a conventional PCM system is tied to the BP data capture system and the BP data capture system is configured to scale the BP data so that the PCM can accurately display a scaled BP characteristic for the patient. Another option is to permit display of the more accurate BP data on a portable device such as a computer tablet/smartphone. In either case the faint BP measurements associated with these two classes of patients can be accurately monitored in situations where conventional PCM systems fail to detect any pressure or inaccurately display the pressure.

Differential BP Sensing (1300)

Figure 13:
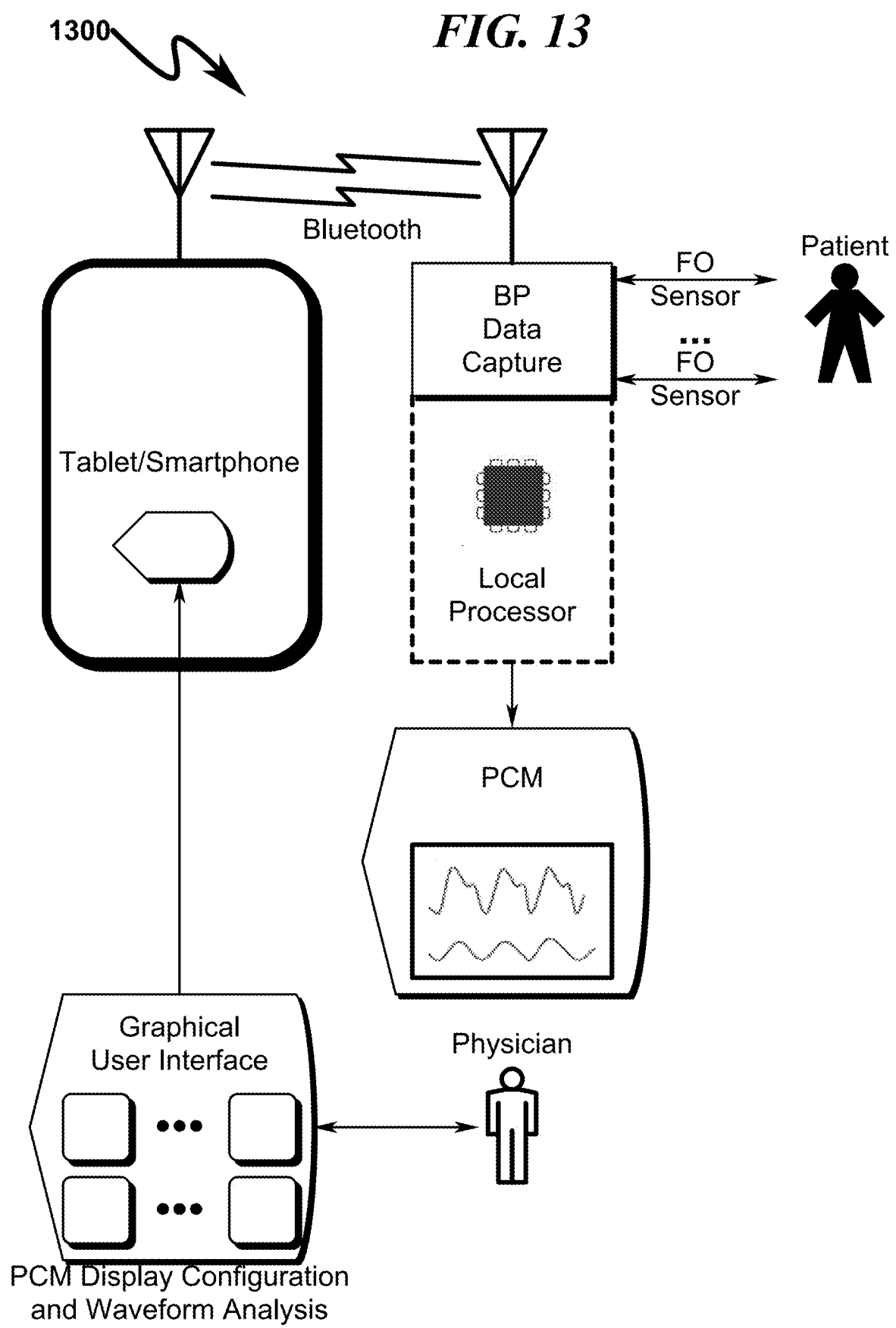
FIG. 13 illustrates an exemplary differential BP sensing system architecture.

As generally illustrated in FIG. 13 (1300), this variant of the BPM system permits multiple BP sensors placed within a patient to be utilized to measure differential blood pressure readings. For example, this might include pressure sensing surrounding a blood clot or other vascular abnormality or in some cases used to determine blood flow rate in some portion of the patient. The high sensitivity and accuracy of the disclosed BP system permits a range of new patient analysis and diagnosis using these spatially diverse BP sensors that is not possible using conventional PCM BPM technologies available today.

Streaming BP Data Analysis (1400)

Figure 14:
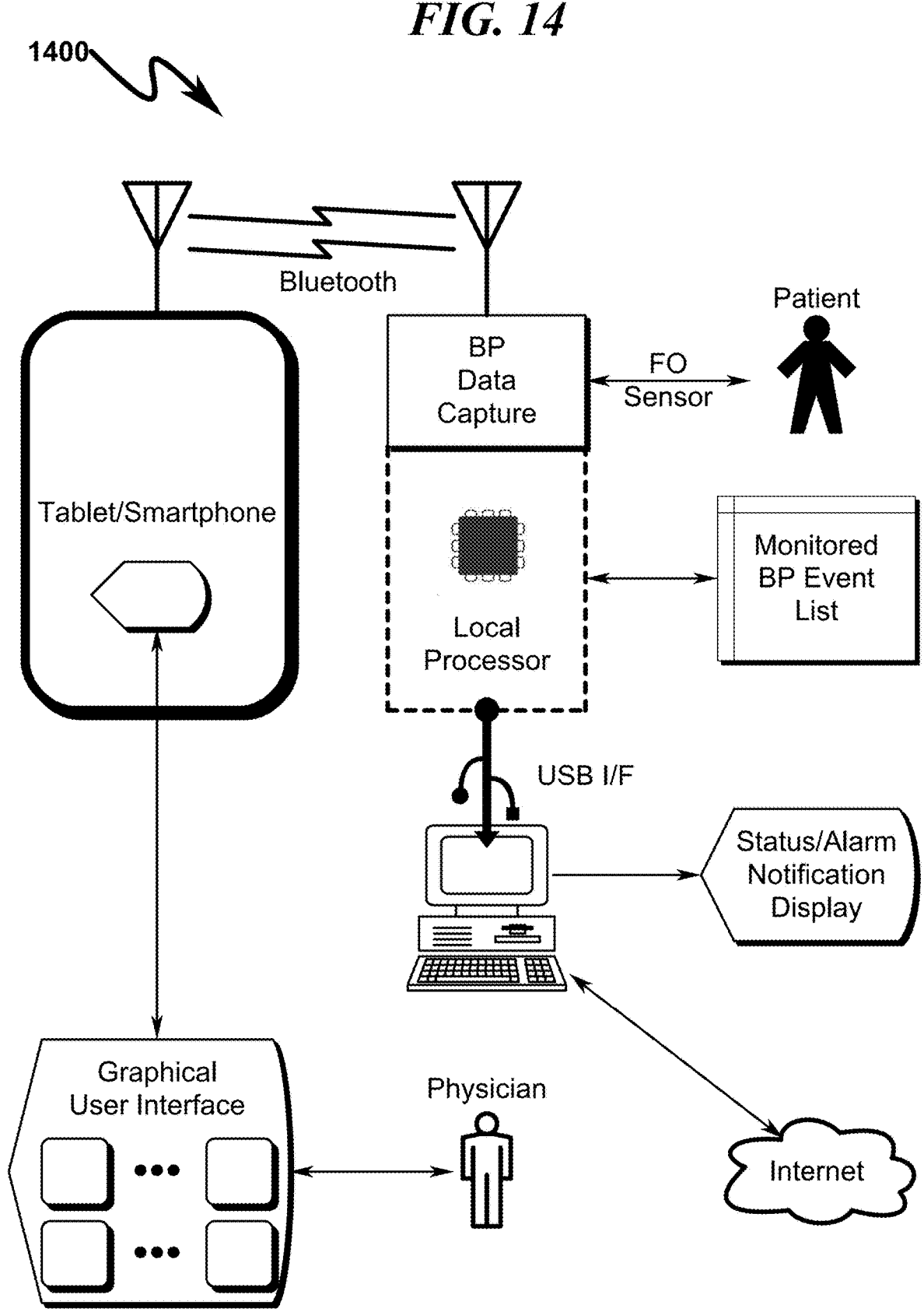
FIG. 14 illustrates an exemplary streaming BP data analysis system architecture.

As generally illustrated in FIG. 14 (1400), this variant of the BPM system as depicted below anticipates that the USB interface associated with the BPM can be used to perform complex analysis of the real-time BP data retrieved from the patient. Since it is not possible to incorporate all the processing/display features desired in an integrated BPM system, the use of a standard PC to perform these analysis functions while streaming real-time BP data from the patient is anticipated. Additional benefits of this approach include the potential to incorporate proactive analysis software to predict potential critical care events for the patient and warn physicians and other healthcare providers of the potential trauma event. This data streaming capability also permits remote diagnosis by other physicians and/or computing systems to be enabled, as well as e-mail/text/pages and other notifications to be generated to remote healthcare professionals if abnormal BP readings are detected in the patient.

Wireless/Remote BPM Access (1500)

Figure 15:
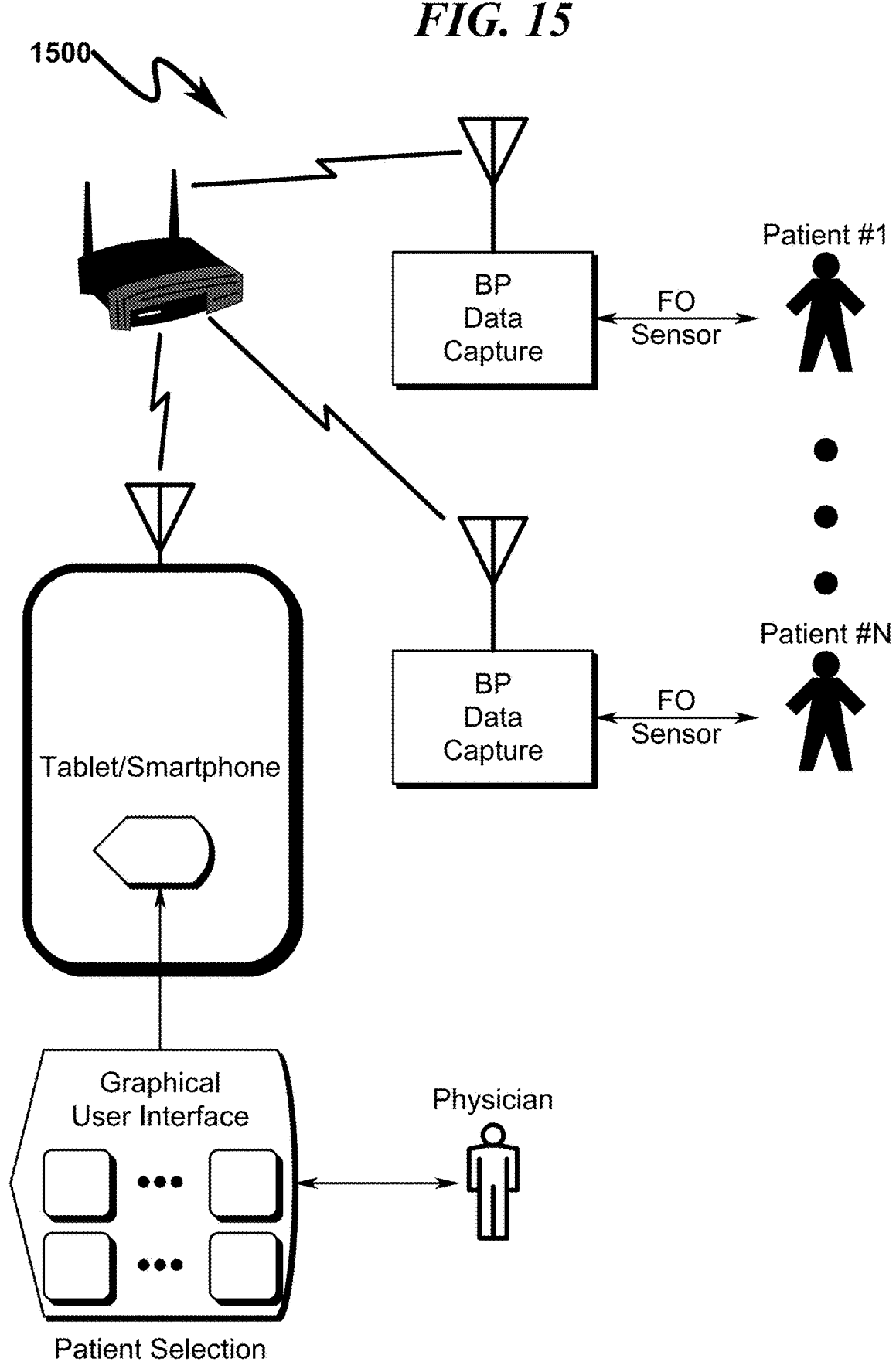
FIG. 15 illustrates an exemplary wireless/remote BPM access system architecture.

As generally illustrated in FIG. 15 (1500), this variant of the BPM system anticipates that a physician may access one or more remote BP systems via a portable device such as a tablet/smartphone. The advantage of this approach is that there is no need to have individual PCM systems for each patient and the physician or other healthcare professional can remotely access the status of any patient via a portable device. This also permits incorporation of sophisticated BP analysis software and other special medical programs within a given portable device which would not be possible using conventional PCM systems.

Customized BP Analysis (1600)

Figure 16:
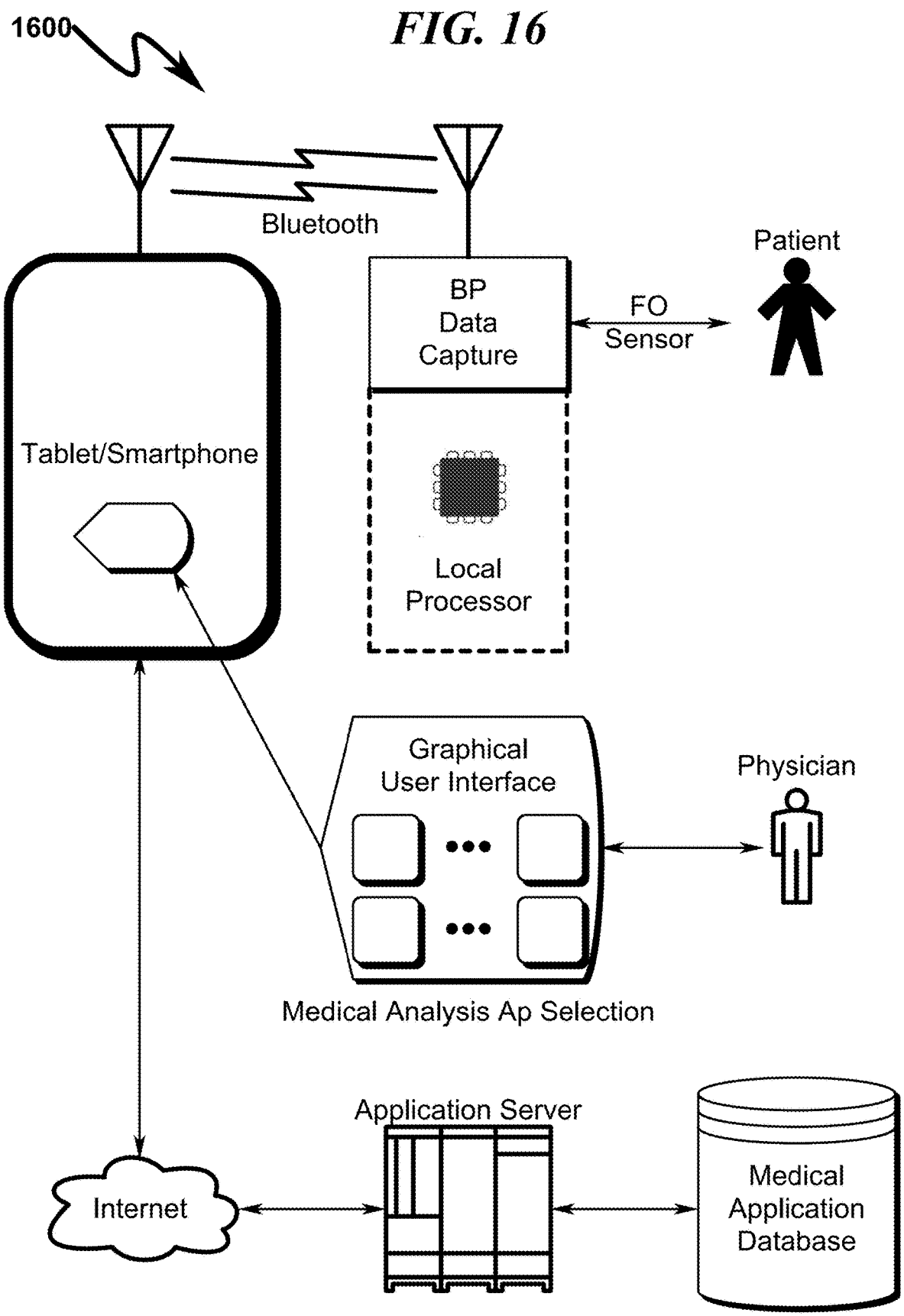
FIG. 16 illustrates an exemplary customized BP analysis system architecture.

As generally illustrated in FIG. 16 (1600), this variant of the BPM system anticipates that a physician will interact with the BP data capture system using a wireless interface to a tablet/smartphone. This will allow the physician to select various software applications from a medical application database served over the Internet. These software applications can operate on the tablet/smartphone but may also download software (as application data files) to the local processor associated with the BP data capture device and thus permit real-time analysis of BP readings from the patient.

System Summary

The present invention system anticipates a wide variety of variations in the basic theme of construction, but can be generalized as a blood pressure analysis system comprising:
 (a) computing device;
 (b) analog sensor A/D converter;
 (c) bridge excitation converter; and
 (d) bridge sense D/A converter;
 wherein
 the analog sensor A/D converter samples an analog signal from an analog sensor and converts the analog signal to a digital sensor value;
 the analog sensor is associated with calibration factors that comprises data used to normalize the analog signal from the analog sensor;
 the computing device applies the calibration factors to the digital sensor value to produce a digital compensated sensor value;
 the bridge excitation converter receives an analog Wheatstone Bridge excitation signal and converts the analog Wheatstone Bridge excitation signal to produce a bridge excitation value;
 the bridge sense D/A converter receives the digital compensated sensor value and generates an analog compensated sensor value; and
 the analog compensated sensor value is scaled by the bridge excitation value to produce a converted analog Wheatstone Bridge sense signal.

This general system summary may be augmented by the various elements described herein to produce a wide variety of invention embodiments consistent with this overall design description.

Method Summary

The present invention method anticipates a wide variety of variations in the basic theme of implementation, but can be generalized as a blood pressure analysis method comprising:
 (1) sampling an output signal from an analog sensor using an A/D converter to produce a digital sensor output value;
 (2) applying calibration factors to the digital sensor output value using a computing device to produce a digital sensor compensated value;
 (3) sensing a Wheatstone Bridge excitation voltage signal to form a bridge excitation value;
 (4) converting the digital sensor compensated value from digital to analog using a D/A converter to produce an analog sensor compensated value; and
 (5) scaling the analog sensor compensated value by the bridge excitation value to produce a converted Wheatstone Bridge sense signal.

This general method may be modified heavily depending on a number of factors, with rearrangement and/or addition/deletion of steps anticipated by the scope of the present invention. Integration of this and other preferred exemplary embodiment methods in conjunction with a variety of preferred exemplary embodiment systems described herein is anticipated by the overall scope of the present invention.

System/Method Variations

The present invention anticipates a wide variety of variations in the basic theme of construction. The examples presented previously do not represent the entire scope of possible usages. They are meant to cite a few of the almost limitless possibilities.

This basic system and method may be augmented with a variety of ancillary embodiments, including but not limited to:
 An embodiment wherein the analog sensor comprises a fiber optic pressure sensor.
 An embodiment wherein the analog sensor comprises a Fabry-Perot pressure sensor.
 An embodiment wherein the analog sensor comprises a Fabry-Perot pressure sensor located within a medical device.
 An embodiment wherein the analog sensor comprises a Fabry-Perot pressure sensor positioned at the distal end of a medical device, the medical device selected from a group consisting of a catheter, catheter incorporating a mounted balloon, vascular sheath, ventriculostomy catheter, ventricular shunt catheter, lumbar drain, and intracranial pressure monitor structure.
 An embodiment wherein the analog sensor comprises a Fabry-Perot pressure sensor positioned proximal to the distal end of a medical device, the medical device selected from a group consisting of a catheter, catheter incorporating a mounted balloon, vascular sheath, ventriculostomy catheter, ventricular shunt catheter, lumbar drain, and intracranial pressure monitor structure.
 An embodiment wherein the analog sensor comprises a plethora of Fabry-Perot pressure sensors located within a medical device, the medical device selected from a group consisting of a catheter, catheter incorporating a mounted balloon, vascular sheath, ventriculostomy catheter, ventricular shunt catheter, lumbar drain, and intracranial pressure monitor structure.

An embodiment wherein the analog sensor is an invasive arterial blood pressure (IBP) sensor.

An embodiment wherein the analog Wheatstone Bridge excitation signal is generated by a patient care monitor (PCM).

An embodiment wherein the converted analog Wheatstone Bridge sense signal is displayed using a patient care monitor (PCM).

An embodiment wherein the analog sensor further comprises a non-volatile memory in which the calibration factors are stored.

An embodiment wherein the analog sensor further comprises a RFID TAG memory in which the calibration factors are stored.

An embodiment wherein the analog sensor is zero calibrated to atmospheric pressure.

An embodiment wherein the digital bridge sense value is transmitted to a display device that indicates systolic blood pressure, diastolic blood pressure, mean blood pressure, and/or heart rate values.

An embodiment wherein the system further comprises a visual status indicator, the visual status indicator displaying a pressure value that is selected from a plethora of the digital compensated sensor values within a sampling period.

An embodiment wherein the system further comprises a visual status indicator, the visual status indicator displaying a pressure value that is computed from an analysis of a plethora of the digital compensated sensor values within a sampling period.

An embodiment wherein the system further comprises a visual status indicator, the visual status indicator displaying a pressure value that is computed from a periodic analysis of a plethora of the digital compensated sensor values within a sampling period.

An embodiment wherein the system further comprises a visual status indicator, the visual status indicator displaying a peak pressure value that is computed from an analysis of a plethora of the digital compensated sensor values within a sampling period.

An embodiment wherein the system further comprises a visual status indicator, the visual status indicator displaying a mean pressure value that is computed from an analysis of a plethora of the digital compensated sensor values within a sampling period.

An embodiment wherein the system further comprises a visual status indicator, the visual status indicator displaying systolic blood pressure, diastolic blood pressure, mean blood pressure, and/or heart rate values that are computed from an analysis of a plethora of the digital compensated sensor values.

An embodiment wherein the digital compensated sensor value is streamed via a hardwired serial interface to a remote computer system for analysis of the digital sensor value derived from the analog sensor.

An embodiment wherein the digital compensated sensor value is streamed via a wireless serial interface to a remote computer system for analysis of the digital sensor value derived from the analog sensor.

An embodiment wherein the analog sensor A/D converter is replicated to permit multichannel input data collection from a plethora of analog sensors; and the computing device comprises multiple digital inputs to enable input processing of data received from the replicated analog sensor A/D converter.

An embodiment wherein the analog sensor A/D converter is replicated to permit multichannel input data collection from a plethora of analog sensors; the bridge excitation converter and the bridge sense D/A converter are replicated and/or multiplexed to permit multichannel data collection; the computing device comprises multiple digital inputs to enable input processing of data received from the replicated analog sensor A/D converter; the computing device comprises multiple digital inputs to enable input processing of data received from the replicated bridge excitation converter; and the computing device comprises multiple digital outputs to enable output processing of data to the replicated bridge sense D/A converter.

An embodiment wherein the scaling of the analog compensated sensor value is accomplished by converting the bridge excitation value from analog to digital using an A/D converter to produce a digital bridge excitation value and combining the digital bridge excitation value with the digital compensated sensor value to generate the converted analog Wheatstone Bridge sense signal.

One skilled in the art will recognize that other embodiments are possible based on combinations of elements taught within the above invention description.

Generalized Computer Usable Medium

In various alternate embodiments, the present invention may be implemented as a computer program product for use with a computerized computing system. Those skilled in the art will readily appreciate that programs defining the functions defined by the present invention can be written in any appropriate programming language and delivered to a computer in many forms, including but not limited to: (a) information permanently stored on non-writeable storage media (e.g., read-only memory devices such as ROMs or CD-ROM disks); (b) information alterably stored on writeable storage media (e.g., floppy disks and hard drives); and/or (c) information conveyed to a computer through communication media, such as a local area network, a telephone network, or a public network such as the Internet. When carrying computer readable instructions that implement the present invention methods, such computer readable media represent alternate embodiments of the present invention.

As generally illustrated herein, the present invention system embodiments can incorporate a variety of computer readable media that comprise computer usable medium having computer readable code means embodied therein. One skilled in the art will recognize that the software associated with the various processes described herein can be embodied in a wide variety of computer accessible media from which the software is loaded and activated. Pursuant to In re Beauregard, 35 USPQ2d 1383 (U.S. Pat. No. 5,710,578), the present invention anticipates and includes this type of computer readable media within the scope of the invention. Pursuant to In re Nuijten, 500 F.3d 1346 (Fed. Cir. 2007) (U.S. patent application Ser. No. 09/211,928), the present invention scope is limited to computer readable media wherein the media is both tangible and non-transitory.

CONCLUSION

A blood pressure analysis system/method allowing conversion from an analog sensor input to a standardized analog output interface has been disclosed. In some preferred embodiments the system/method permits a fiber optic pressure sensor to be interfaced to a standard patient care monitor (PCM) system using standardized Wheatstone Bridge analog interface inputs. Within this context the Wheatstone Bridge sensed output is defined by stimulus from the PCM and modulation of bridge element values by the conditioned output of an analog pressure sensor. The use of analog-to-digital-to-analog conversion in this blood pressure analysis permits retrofitting of PCM devices having analog Wheatstone Bridge inputs with advanced patient monitoring sensors without the need for specialized modifications to the baseline PCM data collection framework. Methods disclosed herein include techniques to connect arbitrary types/numbers of analog sensors to traditional PCM systems without the need for PCM system hardware/software modifications.

CLAIMS

Although a preferred embodiment of the present invention has been illustrated in the accompanying drawings and described in the foregoing Detailed Description, it will be understood that the invention is not limited to the embodiments disclosed, but is capable of numerous rearrangements, modifications, and substitutions without departing from the spirit of the invention as set forth and defined by the following claims.

What is claimed is:

1. A blood pressure analysis system comprising:
   an analog sensor (ASEN) in communication with a fiber optic signal conditioner via a fiber optic connector;
   an intelligent patient monitor interface configured to connect between ASEN and at least one external device, including:
      at least one memory device (TSM) capable of storing a set of calibration factors (CALF), wherein the at least one memory device is housed within the fiber optic connector and wherein the CALF are associated with the ASEN and comprise data that is used with an atmospheric observation to normalize an analog signal (ASIG) from said ASEN;
      a digital signal processor (DSP), wherein the DSP is configured to interact with a user via a user interface to permit selection of at least one analysis algorithm stored in said TSM and that is retrieved by the DSP to be applied to pressure waveforms recorded in said TSM, wherein the at least one analysis algorithm includes selections from averaging, curve fitting, interpolation, extrapolation, peak fitting, peak selection, and mean averaging;
      an analog sensor A/D converter (ADC), where in the ADC is configured to sample said ASIG from said ASEN through a fiber optic signal conditioner in communication with said ASEN by the fiber optic connector and convert said ASIG to a digital sensor value (DSV);
      wherein the DSP is configured to retrieve the CALF from the TSM and apply said CALF to said DSV to produce a digital compensated sensor value (DCV), and the TSM is configured to store a plurality of said DCV and time-stamp data associated with said storage of each of said plurality of said DCV;
      a bridge excitation converter (BEC), wherein the BEC is configured to receive an analog Wheatstone Bridge excitation signal (AWBES) and convert said AWBES to produce a bridge excitation value (BEV);
      a bridge sense D/A converter (DAC), wherein the DAC is configured to receive said DCV and generate an analog compensated sensor value (ACV) and the ACV is scaled by the BEV, wherein the BEV is received by the DAC, to produce a converted analog Wheatstone Bridge sense signal (AWBSS); and
      a blood pressure display (BPD) configured to receive and display results of the at least one analysis algorithm executed by the DSP in real-time and recorded to the TSM.

2. The blood pressure analysis system of claim 1 wherein said ASEN comprises a fiber optic pressure sensor.

3. The blood pressure analysis system of claim 1 wherein said ASEN comprises a Fabry-Perot pressure sensor.

4. The blood pressure analysis system of claim 1 wherein said ASEN comprises a Fabry-Perot pressure sensor located within a medical device.

5. The blood pressure analysis system of claim 1 wherein said ASEN comprises a Fabry-Perot pressure sensor positioned at the distal end of a medical device, said medical device selected from a group consisting of a catheter, catheter incorporating a mounted balloon, vascular sheath, ventriculostomy catheter, ventricular shunt catheter, lumbar drain, and intracranial pressure monitor structure.

6. The blood pressure analysis system of claim 1 wherein said ASEN comprises a plurality of Fabry-Perot pressure sensors located within a medical device, said medical device selected from a group consisting of a catheter, catheter incorporating a mounted balloon, vascular sheath, ventriculostomy catheter, ventricular shunt catheter, lumbar drain, and intracranial pressure monitor structure.

7. The blood pressure analysis system of claim 1 wherein said ASEN is an invasive arterial blood pressure (IBP) sensor.

8. The blood pressure analysis system of claim 1 wherein the system includes the at least one external device, wherein the at least one external device includes a patient care monitor (PCM), and said AWBES is generated by the PCM.

9. The blood pressure analysis system of claim 1 wherein the system includes the at least one external device, wherein the at least one external device includes a patient care monitor (PCM), and said AWBSS is displayed using the PCM.

10. The blood pressure analysis system of claim 1 wherein said ASEN further comprises a non-volatile memory in which said CALF are stored.

11. The blood pressure analysis system of claim 1 wherein said ASEN further comprises a RFID TAG memory in which said CALF are stored.

12. The blood pressure analysis system of claim 1 wherein said ASEN is zero calibrated to atmospheric pressure.

13. The blood pressure analysis system of claim 1 wherein the system includes the at least one external device, wherein the at least one external device includes a display device, wherein said AWBSS is transmitted to the display device that indicates systolic blood pressure, diastolic blood pressure, mean blood pressure, and/or heart rate values.

14. The blood pressure analysis system of claim 1 wherein said system further comprises a visual status indicator (VSI), said VSI configured to display a pressure value that is selected from a plurality of said DCVs within a sampling period.

15. The blood pressure analysis system of claim 1 wherein the system includes the at least one external device, wherein the at least one external device includes a remote computer system, wherein said DCV is streamed via a hardwired serial interface to the remote computer system for analysis of said digital sensor value derived from said ASEN.

16. The blood pressure analysis system of claim 1 wherein
said ADC is replicated to permit multichannel input data collection from a plurality of the analog sensors; and
said DSP comprises multiple digital inputs to enable input processing of data received from said replicated ADC.

17. The blood pressure analysis system of claim 1 wherein
said ADC is replicated to permit multichannel input data collection from a plurality of analog sensors;
said BEC and said DAC are replicated and/or multiplexed to permit multichannel data collection;
said DSP comprises multiple digital inputs to enable input processing of data received from said replicated ADC;
said DSP comprises multiple digital inputs to enable input processing of data received from said replicated BEC; and
said DSP comprises multiple digital outputs to enable output processing of data to said replicated DAC.

18. The blood pressure analysis system of claim 1 wherein said scaling of said ACV is accomplished by converting said BEV from analog to digital using a bridge excitation A/D converter (BDC) to produce a digital bridge excitation value and combining said digital bridge excitation value with said DCV to generate said AWBSS.

19. The blood pressure analysis system of claim 1 wherein said fiber optic signal conditioner is an electro-optical signal conditioner.

20. The blood pressure analysis system of claim 1 wherein said CALF convert measured physical data to absolute pressure values.

21. The blood pressure analysis system of claim 20 wherein said CALF convert measured optical transit delays to absolute pressure values.

22. The blood pressure analysis system of claim 1 further comprising:
said DSP is configured to initiate a zero function prior to insertion of said ASEN into a patient to determine the atmospheric observation.

23. The blood pressure analysis system of claim 1 wherein said analog sensor comprises a Fabry-Perot pressure sensor positioned proximal to the distal end of a medical device, said medical device selected from a group consisting of a catheter, catheter incorporating a mounted balloon, vascular sheath, ventriculostomy catheter, ventricular shunt catheter, lumbar drain, and intracranial pressure monitor structure.

24. The blood pressure analysis system of claim 1 wherein said system further comprises a visual status indicator (VSI), said VSI configured to display a pressure value that is computed from an analysis of a plethora of said DCVs within a sampling period.

25. The blood pressure analysis system of claim 1 wherein said system further comprises a visual status indicator (VSI), said VSI configured to display a pressure value that is computed from a periodic analysis of a plethora of said DCVs within a sampling period.

26. The blood pressure analysis system of claim 1 wherein said system further comprises a visual status indicator (VSI), said VSI configured to display a peak pressure value that is computed from an analysis of a plethora of said DCVs within a sampling period.

27. The blood pressure analysis system of claim 1 wherein said system further comprises a visual status indicator (VSI), said VSI configured to display a mean pressure value that is computed from an analysis of a plethora of said DCVs within a sampling period.

28. The blood pressure analysis system of claim 1 wherein said system further comprises a visual status indicator (VSI), said VSI configured to display systolic blood pressure, diastolic blood pressure, mean blood pressure, and/or heart rate values that are computed from an analysis of a plethora of said DCVs.

29. The blood pressure analysis system of claim 1 wherein the system includes the at least one external device, wherein the at least one external device includes a remote computer, wherein said DCV is streamed via a wireless serial interface to the remote computer system for analysis of said digital sensor value derived from said ASEN.

30. A blood pressure analysis method comprising:
(1) sampling an output signal from an analog sensor (ASEN) using an analog sensor A/D converter (ADC) through a fiber optic signal conditioner that is in communication with the analog sensor via a fiber optic connector that is part of the fiber optic signal conditioner, to produce a digital sensor output value;
(2) retrieving calibration factors (CALF) stored on at least one memory device (TSM) with a digital signal processor (DSP) housed in an intelligent patient monitor interface, wherein the TSM is housed in the fiber optic connector, wherein the intelligent patient monitor interface is configured to connect between ASEN and at least one external device;
(3) applying calibration factors (CALF) to said digital sensor output value using the digital signal processor to produce a digital compensated sensor value (DCV);
(4) storing a plurality of said DCV and time-stamp data associated with each of said plurality of said DCV in said TSM of the intelligent patient monitor interface;
(5) selecting at least one analysis algorithm with a user interface of the intelligent patient monitor interface, wherein said at least one analysis algorithm is configured to be retrieved by said DSP and to be applied to pressure waveforms recorded in the TSM, wherein the at least one analysis algorithm are stored in TSM and includes selections from averaging, curve fitting, interpolation, extrapolation, peak fitting, peak selection, and mean averaging;
(6) applying in real-time said at least one analysis algorithm with said DSP to said pressure waveforms recorded in the TSM and displaying results of said at least one analysis algorithm on a blood pressure display (BPD) of the user interface;
(7) sensing an analog Wheatstone Bridge excitation signal (AWBES) to form a bridge excitation value (BEV) with the intelligent patient monitor interface;
(8) converting said DCV from digital to analog using a D/A converter in the intelligent patient monitor interface to produce an analog compensated sensor value (ACV); and
(9) scaling said ACV by said BEV to produce an analog Wheatstone Bridge sense signal (AWBSS), that is output by the intelligent patient monitor interface.

31. The blood pressure analysis method of claim 30 wherein said ASEN comprises a fiber optic pressure sensor.

32. The blood pressure analysis method of claim 30 wherein said ASEN comprises a Fabry-Perot pressure sensor.

33. The blood pressure analysis method of claim 30 wherein said ASEN comprises a Fabry-Perot pressure sensor located within a medical device.

34. The blood pressure analysis method of claim 30 wherein said ASEN comprises a Fabry-Perot pressure sensor positioned at the distal end of a medical device, said medical device selected from a group consisting of a catheter, catheter incorporating a mounted balloon, vascular sheath, ventriculostomy catheter, ventricular shunt catheter, lumbar drain, and intracranial pressure monitor structure.

35. The blood pressure analysis method of claim 30 wherein said ASEN comprises a plurality of the Fabry-Perot pressure sensors located within a medical device, said medical device selected from a group consisting of a catheter, catheter incorporating a mounted balloon, vascular sheath, ventriculostomy catheter, ventricular shunt catheter, lumbar drain, and intracranial pressure monitor structure.

36. The blood pressure analysis method of claim 30 wherein said ASEN is an invasive arterial blood pressure (IBP) sensor.

37. The blood pressure analysis method of claim 30 wherein the at least one external device includes a patient care monitor (PCM), wherein said AWBES is generated by the PCM.

38. The blood pressure analysis method of claim 30 wherein the at least one external device includes a patient care monitor (PCM), wherein said AWBSS is displayed using the PCM.

39. The blood pressure analysis method of claim 30 wherein said ASEN further comprises a non-volatile memory in which said CALF are stored.

40. The blood pressure analysis method of claim 30 wherein said ASEN further comprises a RFID TAG memory in which said CALF are stored.

41. The blood pressure analysis method of claim 30 wherein said ASEN is zero calibrated to atmospheric pressure.

42. The blood pressure analysis method of claim 30 wherein the at least one external device includes a display device, wherein said AWBSS is transmitted to the display device that indicates systolic blood pressure, diastolic blood pressure, mean blood pressure, and/or heart rate values.

43. The blood pressure analysis method of claim 30 further comprising using a visual status indicator (VSI), said VSI configured to display a pressure value that is selected from a plurality of said DCVs within a sampling period.

44. The blood pressure analysis method of claim 30 wherein the at least one external device includes a remote computer system, wherein said DCV is streamed via a hardwired serial interface to the remote computer system for analysis of said digital sensor output value derived from said ASEN.

45. The blood pressure analysis method of claim 30 further comprising
  replicating said ADC to permit multichannel input data collection from a plurality of the analog sensors; and
  said DSP comprises multiple digital inputs to enable input processing of data received from said replicated ADC.

46. The blood pressure analysis method of claim 30 further comprising
  replicating said ADC to permit multichannel input data collection from a plurality of analog sensors;
  replicating and/or multiplexing said BEC and said DAC to permit multichannel data collection;
  said DSP comprises multiple digital inputs to enable input processing of data received from said replicated ADC;
  said DSP comprises multiple digital inputs to enable input processing of data received from said replicated and/or multiplexed BEC; and
  said DSP comprises multiple digital outputs to enable output processing of data to said replicated and/or multiplexed DAC.

47. The blood pressure analysis method of claim 30 wherein said scaling of said ACV is accomplished by converting said BEV from analog to digital using a bridge excitation A/D converter (BDC) to produce a digital bridge excitation value and combining said digital bridge excitation value with said DCV to generate said AWBSS.

48. The blood pressure analysis method of claim 30 wherein said fiber optic signal conditioner is an electro-optical signal conditioner.

49. The blood pressure analysis method of claim 30 wherein said CALF are associated with said ASEN and convert measured physical data to absolute pressure values.

50. The blood pressure analysis method of claim 49 wherein said CALF convert measured optical transit delays to absolute pressure values.

51. The blood pressure analysis method of claim 30 further comprising: initiating a zero function with the digital signal processor (DSP) prior to inserting the analog sensor (ASEN) into a patient to determine an atmospheric observation.

52. The blood pressure analysis method of claim 51, wherein applying calibration factors (CALF) further comprises incorporating the atmospheric observation.

53. The blood pressure analysis method of claim 30 wherein said ASEN comprises a Fabry-Perot pressure sensor positioned proximal to the distal end of a medical device, said medical device selected from a group consisting of a catheter, catheter incorporating a mounted balloon, vascular sheath, ventriculostomy catheter, ventricular shunt catheter, lumbar drain, and intracranial pressure monitor structure.

54. The blood pressure analysis method of claim 30 further comprising using a visual status indicator (VSI), said VSI configured to display a pressure value that is computed from an analysis of a plethora of said DCVs within a sampling period.

55. The blood pressure analysis method of claim 30 further comprising using a visual status indicator (VSI), said VSI configured to display a pressure value that is computed from a periodic analysis of a plethora of said DCVs within a sampling period.

56. The blood pressure analysis method of claim 30 further comprising using a visual status indicator (VSI), said VSI configured to display a peak pressure value that is computed from an analysis of a plethora of said DCVs within a sampling period.

57. The blood pressure analysis method of claim 30 further comprising using a visual status indicator (VSI), said VSI configured to display a mean pressure value that is computed from an analysis of a plethora of said DCVs within a sampling period.

58. The blood pressure analysis method of claim 30 further comprising using a visual status indicator (VSI), said VSI configured to display systolic blood pressure, diastolic blood pressure, mean blood pressure, and/or heart rate values that are computed from an analysis of a plethora of said DCVs.

59. The blood pressure analysis method of claim 30 wherein at least one external device includes a remote computer system, wherein said DCV is streamed via a wireless serial interface to the remote computer system for analysis of said digital sensor output value derived from said ASEN.

* * * * *